(12) United States Patent
Sibbitt, Jr. et al.

(10) Patent No.: US 9,456,811 B2
(45) Date of Patent: Oct. 4, 2016

(54) VASCULAR CLOSURE METHODS AND APPARATUSES

(75) Inventors: Wilmer L. Sibbitt, Jr., Albuquerque, NM (US); Randy R. Sibbitt, Helena, MT (US)

(73) Assignee: ABBOTT VASCULAR INC., Santa Clara, CA (US)

( * ) Notice: Subject to any disclaimer, the term of this patent is extended or adjusted under 35 U.S.C. 154(b) by 1207 days.

(21) Appl. No.: 11/508,715

(22) Filed: Aug. 23, 2006

(65) Prior Publication Data

US 2007/0203506 A1    Aug. 30, 2007

Related U.S. Application Data

(63) Continuation-in-part of application No. 11/316,775, filed on Dec. 23, 2005, now abandoned.

(60) Provisional application No. 60/711,279, filed on Aug. 24, 2005.

(51) Int. Cl.
| | |
|---|---|
| *A61B 17/00* | (2006.01) |
| *A61B 17/12* | (2006.01) |
| *A61B 17/06* | (2006.01) |
| *A61B 17/04* | (2006.01) |

(52) U.S. Cl.
CPC ...... *A61B 17/0057* (2013.01); *A61B 17/06066* (2013.01); *A61B 17/12* (2013.01); *A61B 17/12009* (2013.01); *A61B 17/12013* (2013.01); *A61B 2017/00349* (2013.01); *A61B 2017/00663* (2013.01); *A61B 2017/00668* (2013.01); *A61B 2017/0475* (2013.01); *A61B 2017/06176* (2013.01); *A61B 2017/12018* (2013.01)

(58) Field of Classification Search
CPC ............ A61B 17/12; A61B 17/12009; A61B 17/12013; A61B 17/32056; A61B 2017/12004; A61B 2017/0477; A61B 2017/12018; A61B 2017/0475
USPC .................. 606/113, 139, 144, 148, 151, 228
See application file for complete search history.

(56) References Cited

U.S. PATENT DOCUMENTS

| | | |
|---|---|---|
| 287,046 A | 10/1883 | Norton |
| 312,408 A | 2/1885 | Wackerhagen |
| 438,400 A | 10/1890 | Brennen |
| 597,165 A | 1/1898 | Hall |
| 659,422 A | 10/1900 | Shidler |

(Continued)

FOREIGN PATENT DOCUMENTS

| | | |
|---|---|---|
| CA | 2 339 060 | 2/2000 |
| DE | 912619 | 5/1854 |

(Continued)

OTHER PUBLICATIONS

U.S. Appl. No. 90/006,469, filed Nov. 29, 2002, Modesitt et al.

(Continued)

*Primary Examiner* — Dianne Dornbusch
(74) *Attorney, Agent, or Firm* — Workman Nydegger; Randy Shen

(57) ABSTRACT

A vascular closure device comprised of a sheath-delivered cincture or noose-like device or knot comprised of suture, wire, or other suitable materials, that is placed on the external surface of a puncture wound, and closed. The vascular closure cincture is delivered by a sheath, and after closing is left resident on the external surface of a tissue puncture wound.

24 Claims, 8 Drawing Sheets

(56) References Cited

U.S. PATENT DOCUMENTS

| | | |
|---|---|---|
| 989,231 A | 4/1911 | Davis |
| 1,088,393 A | 2/1914 | Backus |
| 1,242,139 A | 10/1917 | Callahan |
| 1,331,401 A | 2/1920 | Summers |
| 1,574,362 A | 9/1922 | Callahan |
| 1,480,935 A | 1/1924 | Gleason |
| 1,596,004 A | 8/1926 | De Bengoa |
| 1,625,602 A | 4/1927 | Gould et al. |
| 1,647,958 A | 11/1927 | Ciarlante |
| 1,880,569 A | 10/1932 | Weis |
| 1,940,351 A | 3/1933 | Howard |
| 2,012,776 A | 8/1935 | Roeder |
| 2,087,074 A | 7/1937 | Tucker |
| 2,131,321 A | 10/1937 | Hart |
| 2,108,206 A | 2/1938 | Meeker |
| 2,127,903 A | 7/1938 | Bowen |
| 2,254,620 A | 9/1941 | Miller |
| 2,316,297 A | 4/1943 | Southerland et al. |
| 2,371,978 A | 3/1945 | Perham |
| 2,397,823 A | 4/1946 | Walter |
| RE22,857 E | 3/1947 | Ogburn |
| 2,453,227 A | 11/1948 | James |
| 2,595,086 A | 11/1948 | Larzelere |
| 2,583,625 A | 1/1952 | Bergan |
| 2,588,589 A | 3/1952 | Tauber |
| 2,610,631 A * | 9/1952 | Calicchio ............ 606/139 |
| 2,646,045 A | 7/1953 | Priestley |
| 2,684,070 A | 7/1954 | Kelsey |
| 2,692,599 A | 10/1954 | Creelman |
| 2,910,067 A | 10/1959 | White |
| 2,941,489 A | 6/1960 | Fischbein |
| 2,944,311 A | 7/1960 | Schneckenberger |
| 2,951,482 A | 9/1960 | Sullivan |
| 2,959,172 A | 11/1960 | Held |
| 2,969,887 A | 1/1961 | Darmstadt et al. |
| 3,015,403 A | 1/1962 | Fuller |
| 3,033,156 A | 5/1962 | Verlish |
| 3,104,666 A | 9/1963 | Hale et al. |
| 3,113,379 A | 12/1963 | Frank |
| 3,120,230 A | 2/1964 | Skold |
| 3,142,878 A | 8/1964 | Santora |
| 3,197,102 A | 7/1965 | Bates et al. |
| 3,209,754 A | 10/1965 | Brown |
| 3,348,595 A | 10/1967 | Stevens, Jr. |
| 3,357,070 A | 12/1967 | Sloan |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,482,428 A | 12/1969 | Kapitanov et al. |
| 3,494,533 A | 2/1970 | Green et al. |
| 3,523,351 A | 8/1970 | Filia |
| 3,586,002 A | 6/1971 | Wood et al. |
| 3,587,115 A | 6/1971 | Shiley |
| 3,604,425 A | 9/1971 | Le Roy |
| 3,618,447 A | 11/1971 | Goins |
| 3,630,205 A | 12/1971 | Listner |
| 3,653,388 A | 4/1972 | Tenckhoff |
| 3,665,926 A | 5/1972 | Flores |
| 3,677,243 A | 7/1972 | Nerz |
| 3,682,180 A | 8/1972 | McFarlane |
| 3,757,629 A | 9/1973 | Schneider |
| 3,760,810 A * | 9/1973 | Van Hoorn ............ 606/140 |
| 3,776,237 A | 12/1973 | Hill et al. |
| 3,802,438 A | 4/1974 | Wolvek |
| 3,805,337 A | 4/1974 | Branstetter |
| 3,814,104 A | 6/1974 | Irnich et al. |
| 3,820,544 A | 6/1974 | Semm |
| 3,828,791 A | 8/1974 | Santos |
| 3,840,017 A | 10/1974 | Violante |
| 3,856,016 A | 12/1974 | Davis |
| 3,856,018 A | 12/1974 | Perisse et al. |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,944,114 A | 3/1976 | Coppens |
| 3,985,138 A | 10/1976 | Jarvik |
| 4,011,872 A | 3/1977 | Komiya |
| 4,014,492 A | 3/1977 | Rothfuss |
| 4,018,228 A | 4/1977 | Goosen |
| 4,018,229 A * | 4/1977 | Komiya ............ 606/139 |
| 4,064,881 A | 12/1977 | Meredith |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,162,673 A | 7/1979 | Patel |
| 4,168,073 A | 9/1979 | LaRue |
| 4,169,476 A | 10/1979 | Hiltebrandt |
| 4,182,339 A | 1/1980 | Hardy, Jr. |
| 4,185,636 A | 1/1980 | Gabbay et al. |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,216,776 A | 8/1980 | Downie et al. |
| 4,217,665 A | 8/1980 | Bex et al. |
| 4,217,902 A | 8/1980 | March |
| 4,235,177 A | 11/1980 | Arbuckle |
| 4,235,238 A | 11/1980 | Ogiu et al. |
| 4,267,995 A | 5/1981 | McMillan |
| 4,278,091 A | 7/1981 | Borzone |
| 4,316,469 A | 2/1982 | Kapitanov |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,437,465 A | 3/1984 | Nomoto et al. |
| 4,440,170 A | 4/1984 | Golden et al. |
| 4,469,101 A | 9/1984 | Coleman et al. |
| 4,480,356 A | 11/1984 | Martin |
| 4,485,816 A | 12/1984 | Krumme |
| 4,492,229 A | 1/1985 | Grunwald |
| 4,493,323 A | 1/1985 | Albright et al. |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Vaillancourt |
| 4,526,174 A | 7/1985 | Froehlich |
| 4,553,543 A | 11/1985 | Amarasinghe |
| 4,586,503 A | 5/1986 | Kirsch et al. |
| 4,586,614 A | 5/1986 | Ger |
| 4,587,969 A | 5/1986 | Gillis |
| 4,592,498 A | 6/1986 | Braun et al. |
| 4,596,559 A | 6/1986 | Fleischhacker |
| 4,607,638 A | 8/1986 | Crainich |
| 4,610,248 A | 9/1986 | Rosenberg |
| 4,610,251 A | 9/1986 | Kumar |
| 4,610,252 A | 9/1986 | Catalano |
| 4,629,450 A | 12/1986 | Suzuki et al. |
| 4,635,634 A | 1/1987 | Santos |
| 4,651,733 A | 3/1987 | Mobin-Uddin |
| 4,655,211 A | 4/1987 | Sakamoto et al. |
| 4,665,906 A | 5/1987 | Jervis |
| 4,687,469 A | 8/1987 | Osypka |
| 4,697,312 A | 10/1987 | Freyer |
| 4,702,250 A | 10/1987 | Ovil et al. |
| 4,719,917 A | 1/1988 | Barrows et al. |
| 4,723,549 A | 2/1988 | Wholey et al. |
| 4,724,840 A | 2/1988 | McVay et al. |
| 4,738,658 A | 4/1988 | Magro et al. |

(56) References Cited

U.S. PATENT DOCUMENTS

| | | |
|---|---|---|
| 4,738,666 A | 4/1988 | Fuqua |
| 4,744,364 A | 5/1988 | Kensey |
| 4,747,407 A | 5/1988 | Liu et al. |
| 4,748,982 A | 6/1988 | Horzewski et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,803,984 A | 2/1989 | Narayanan et al. |
| 4,830,002 A | 5/1989 | Semm |
| 4,832,688 A | 5/1989 | Sagae et al. |
| 4,836,204 A | 6/1989 | Landymore et al. |
| 4,836,205 A | 6/1989 | Barrett |
| 4,848,341 A | 7/1989 | Ahmad |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,898,155 A | 2/1990 | Ovil et al. |
| 4,902,508 A | 2/1990 | Badylak et al. |
| 4,911,164 A | 3/1990 | Roth |
| 4,917,087 A | 4/1990 | Walsh et al. |
| 4,917,089 A | 4/1990 | Sideris |
| 4,926,860 A | 5/1990 | Stice et al. |
| 4,929,240 A | 5/1990 | Kirsch et al. |
| 4,929,246 A | 5/1990 | Sinofsky |
| 4,934,364 A | 6/1990 | Green |
| 4,935,027 A | 6/1990 | Yoon |
| 4,950,258 A | 8/1990 | Kawai et al. |
| 4,950,285 A | 8/1990 | Wilk |
| 4,957,498 A | 9/1990 | Caspari et al. |
| 4,957,499 A | 9/1990 | Lipatov et al. |
| 4,961,729 A | 10/1990 | Vaillancourt |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 4,997,436 A | 3/1991 | Oberlander |
| 4,997,439 A | 3/1991 | Chen |
| 5,002,562 A | 3/1991 | Oberlander |
| 5,002,563 A | 3/1991 | Pyka et al. |
| 5,007,921 A | 4/1991 | Brown |
| 5,009,643 A | 4/1991 | Reich et al. |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,037,433 A | 8/1991 | Wilk et al. |
| 5,041,129 A | 8/1991 | Hayhurst et al. |
| 5,047,039 A | 9/1991 | Avant et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,078,731 A | 1/1992 | Hayhurst |
| 5,080,664 A | 1/1992 | Jain |
| 5,092,941 A | 3/1992 | Miura |
| 5,100,418 A | 3/1992 | Yoon et al. |
| 5,100,419 A | 3/1992 | Ehlers |
| 5,100,422 A | 3/1992 | Berguer et al. |
| 5,100,432 A | 3/1992 | Matsutani |
| 5,108,420 A | 4/1992 | Marks |
| 5,108,421 A | 4/1992 | Fowler |
| 5,109,780 A | 5/1992 | Slouf et al. |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,129,882 A | 7/1992 | Weldon et al. |
| 5,129,912 A | 7/1992 | Noda et al. |
| 5,129,913 A | 7/1992 | Ruppert |
| 5,131,379 A | 7/1992 | Sewell, Jr. |
| 5,133,360 A * | 7/1992 | Spears ............... 600/567 |
| 5,144,961 A | 9/1992 | Chen et al. |
| 5,147,373 A | 9/1992 | Ferzli |
| 5,147,381 A | 9/1992 | Heimerl et al. |
| 5,156,609 A | 10/1992 | Nakao et al. |
| 5,156,788 A | 10/1992 | Chesterfield et al. |
| 5,160,339 A | 11/1992 | Chen et al. |
| 5,163,946 A | 11/1992 | Li |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,691 A * | 1/1993 | Pierce ............... 606/148 |
| 5,178,629 A | 1/1993 | Kammerer |
| 5,192,287 A * | 3/1993 | Fournier et al. ............... 606/139 |
| 5,192,288 A | 3/1993 | Thompson et al. |
| 5,192,294 A | 3/1993 | Blake, III |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,201,744 A | 4/1993 | Jones |
| 5,207,703 A | 5/1993 | Jain |
| 5,209,756 A | 5/1993 | Seedhom et al. |
| 5,211,650 A | 5/1993 | Noda |
| 5,217,024 A | 6/1993 | Dorsey et al. |
| 5,217,470 A | 6/1993 | Weston |
| 5,217,471 A * | 6/1993 | Burkhart ............... 606/148 |
| 5,217,485 A | 6/1993 | Liv et al. |
| 5,219,358 A | 6/1993 | Bendel et al. |
| 5,222,974 A | 6/1993 | Kensey et al. |
| 5,226,908 A | 7/1993 | Yoon |
| 5,234,443 A | 8/1993 | Phan et al. |
| 5,234,445 A | 8/1993 | Walker et al. |
| 5,236,435 A | 8/1993 | Sewell, Jr. |
| 5,237,996 A | 8/1993 | Waldman et al. |
| 5,242,427 A | 9/1993 | Bilweis |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,033 A | 10/1993 | Evans et al. |
| 5,250,053 A | 10/1993 | Snyder |
| 5,250,054 A | 10/1993 | Li |
| 5,250,058 A | 10/1993 | Miller et al. |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,269,792 A | 12/1993 | Kovac et al. |
| 5,275,616 A | 1/1994 | Fowler |
| 5,279,311 A | 1/1994 | Snyder |
| 5,281,236 A | 1/1994 | Bagnato et al. |
| 5,281,237 A | 1/1994 | Gimpelson |
| 5,281,422 A | 1/1994 | Badylak et al. |
| 5,282,808 A | 2/1994 | Kovac et al. |
| 5,282,827 A | 2/1994 | Kensey et al. |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,243 A | 3/1994 | Chodorow et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | Van Tassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,078 A * | 4/1994 | Buelna ............... 606/113 |
| 5,300,085 A | 4/1994 | Yock |

(56) References Cited

U.S. PATENT DOCUMENTS

| | | | |
|---|---|---|---|
| 5,304,184 A | | 4/1994 | Hathaway et al. |
| 5,304,185 A | | 4/1994 | Taylor |
| 5,304,204 A | | 4/1994 | Bregen |
| 5,306,254 A | | 4/1994 | Nash et al. |
| 5,312,024 A | | 5/1994 | Grant et al. |
| 5,312,423 A | | 5/1994 | Rosenbluth et al. |
| 5,318,542 A | | 6/1994 | Hirsch et al. |
| 5,318,578 A | | 6/1994 | Hasson |
| 5,320,629 A | | 6/1994 | Noda et al. |
| 5,320,632 A | | 6/1994 | Heidmueller |
| 5,320,639 A | | 6/1994 | Rudnick |
| 5,330,445 A | | 7/1994 | Haaga |
| 5,330,491 A | | 7/1994 | Walker et al. |
| 5,334,216 A | | 8/1994 | Vidal et al. |
| 5,334,217 A | | 8/1994 | Das |
| 5,335,680 A | | 8/1994 | Moore |
| 5,336,229 A | | 8/1994 | Noda |
| 5,336,230 A | | 8/1994 | Leichtling et al. |
| 5,336,231 A | * | 8/1994 | Adair .................. 606/148 |
| 5,340,360 A | | 8/1994 | Stefanchik |
| 5,342,369 A | | 8/1994 | Harryman, II |
| 5,350,399 A | | 9/1994 | Erlebacher et al. |
| 5,352,229 A | | 10/1994 | Goble et al. |
| 5,354,279 A | | 10/1994 | Hofling |
| 5,354,312 A | | 10/1994 | Brinkerhoff et al. |
| 5,364,406 A | | 11/1994 | Sewell, Jr. |
| 5,364,407 A | | 11/1994 | Poll |
| 5,364,408 A | | 11/1994 | Gordon |
| 5,366,458 A | | 11/1994 | Korthoff et al. |
| 5,366,479 A | | 11/1994 | McGarry et al. |
| 5,368,595 A | | 11/1994 | Lewis |
| 5,368,601 A | | 11/1994 | Sauer et al. |
| 5,374,275 A | | 12/1994 | Bradley et al. |
| 5,374,278 A | | 12/1994 | Chesterfield et al. |
| 5,376,096 A | | 12/1994 | Foster |
| 5,383,896 A | | 1/1995 | Gershony et al. |
| 5,383,905 A | * | 1/1995 | Golds et al. .................. 606/232 |
| 5,385,569 A | | 1/1995 | Swor |
| RE34,866 E | | 2/1995 | Kensey et al. |
| 5,387,221 A | | 2/1995 | Bisgaard |
| 5,387,227 A | | 2/1995 | Grice |
| 5,391,176 A | | 2/1995 | de la Torre |
| 5,391,182 A | | 2/1995 | Chin |
| 5,392,978 A | | 2/1995 | Velez et al. |
| 5,395,030 A | | 3/1995 | Kuramoto et al. |
| 5,395,332 A | | 3/1995 | Ressemann et al. |
| 5,395,349 A | | 3/1995 | Quiachon et al. |
| 5,397,310 A | | 3/1995 | Chu et al. |
| 5,397,325 A | | 3/1995 | Della Badia et al. |
| 5,397,326 A | | 3/1995 | Mangum |
| 5,403,329 A | | 4/1995 | Hinchcliffe |
| 5,403,330 A | * | 4/1995 | Tuason .................. 606/148 |
| 5,403,331 A | * | 4/1995 | Chesterfield et al. ........ 606/148 |
| 5,403,338 A | | 4/1995 | Milo |
| 5,404,621 A | | 4/1995 | Heinke |
| 5,411,481 A | | 5/1995 | Allen et al. |
| 5,411,520 A | | 5/1995 | Nash et al. |
| 5,413,571 A | | 5/1995 | Katsaros et al. |
| 5,413,584 A | | 5/1995 | Schulze |
| 5,416,584 A | | 5/1995 | Kay |
| 5,417,699 A | | 5/1995 | Klein et al. |
| 5,419,765 A | | 5/1995 | Weldon et al. |
| 5,419,777 A | | 5/1995 | Hofling |
| 5,423,857 A | | 6/1995 | Rosenman et al. |
| 5,425,489 A | | 6/1995 | Shichman et al. |
| 5,425,705 A | | 6/1995 | Evard et al. |
| 5,425,740 A | | 6/1995 | Hutchinson, Jr. |
| 5,431,639 A | | 7/1995 | Shaw |
| 5,431,666 A | | 7/1995 | Sauer et al. |
| 5,431,667 A | | 7/1995 | Thompson et al. |
| 5,433,700 A | | 7/1995 | Peters |
| 5,433,721 A | | 7/1995 | Hooven et al. |
| 5,437,631 A | | 8/1995 | Janzen |
| 5,439,479 A | | 8/1995 | Shichman et al. |
| 5,443,477 A | | 8/1995 | Marin et al. |
| 5,443,481 A | | 8/1995 | Lee |
| 5,449,359 A | | 9/1995 | Groiso |
| 5,452,733 A | | 9/1995 | Sterman et al. |
| 5,454,822 A | | 10/1995 | Schob et al. |
| 5,454,834 A | | 10/1995 | Boebel et al. |
| 5,456,400 A | | 10/1995 | Shichman et al. |
| 5,458,574 A | | 10/1995 | Machold et al. |
| 5,462,560 A | | 10/1995 | Stevens |
| 5,462,561 A | | 10/1995 | Voda |
| 5,464,426 A | | 11/1995 | Bonutti |
| 5,466,241 A | * | 11/1995 | Leroy et al. .................. 606/139 |
| 5,470,010 A | | 11/1995 | Rothfuss et al. |
| 5,470,338 A | | 11/1995 | Whitfield et al. |
| 5,474,557 A | | 12/1995 | Mai |
| 5,476,469 A | | 12/1995 | Hathaway et al. |
| 5,476,470 A | | 12/1995 | Fitzgibbons, Jr. |
| 5,478,309 A | | 12/1995 | Sweezer et al. |
| 5,478,352 A | | 12/1995 | Fowler |
| 5,478,353 A | | 12/1995 | Yoon et al. |
| 5,478,354 A | | 12/1995 | Tovey et al. |
| 5,480,407 A | | 1/1996 | Wan et al. |
| 5,486,186 A | * | 1/1996 | Yoon .................. 606/148 |
| 5,486,190 A | | 1/1996 | Green |
| 5,486,195 A | | 1/1996 | Myers et al. |
| 5,489,288 A | * | 2/1996 | Buelna .................. 606/144 |
| 5,489,295 A | | 2/1996 | Piplani et al. |
| 5,492,119 A | | 2/1996 | Abrams |
| 5,496,332 A | | 3/1996 | Sierra et al. |
| 5,497,933 A | | 3/1996 | DeFonzo et al. |
| 5,507,744 A | | 4/1996 | Tay et al. |
| 5,507,755 A | | 4/1996 | Gresl et al. |
| 5,507,757 A | | 4/1996 | Sauer et al. |
| 5,507,758 A | | 4/1996 | Thomason et al. |
| 5,509,902 A | | 4/1996 | Raulerson |
| 5,520,655 A | | 5/1996 | Davila et al. |
| 5,520,665 A | | 5/1996 | Fleetwood |
| 5,520,702 A | | 5/1996 | Sauer et al. |
| 5,522,840 A | | 6/1996 | Krajicek |
| 5,527,321 A | | 6/1996 | Hinchliffe |
| 5,527,322 A | | 6/1996 | Klein et al. |
| D372,310 S | | 7/1996 | Hartnett |
| 5,531,700 A | | 7/1996 | Moore et al. |
| 5,536,251 A | | 7/1996 | Evard et al. |
| 5,536,267 A | | 7/1996 | Edwards et al. |
| 5,536,273 A | | 7/1996 | Lehrer |
| 5,540,701 A | | 7/1996 | Sharkey et al. |
| 5,540,704 A | | 7/1996 | Gordon et al. |
| 5,540,712 A | | 7/1996 | Kleshinski et al. |
| 5,540,716 A | | 7/1996 | Hlavacek |
| 5,544,802 A | | 8/1996 | Crainich |
| 5,545,171 A | | 8/1996 | Sharkey et al. |
| 5,545,178 A | | 8/1996 | Kensey et al. |
| 5,545,180 A | | 8/1996 | Le et al. |
| 5,547,474 A | | 8/1996 | Kloeckl et al. |
| 5,549,618 A | | 8/1996 | Fleenor et al. |
| 5,549,631 A | | 8/1996 | Bonutti |
| 5,554,162 A | | 9/1996 | DeLange |
| 5,560,532 A | | 10/1996 | DeFonzo et al. |
| 5,562,684 A | * | 10/1996 | Kammerer .................. 606/139 |
| 5,562,686 A | | 10/1996 | Sauer et al. |
| 5,562,688 A | | 10/1996 | Riza |
| 5,562,728 A | | 10/1996 | Lazarus et al. |
| 5,567,435 A | | 10/1996 | Hubbell et al. |
| 5,569,269 A | | 10/1996 | Hart et al. |
| 5,569,271 A | | 10/1996 | Hoel |
| 5,571,120 A | * | 11/1996 | Yoon .................. 606/148 |
| 5,573,540 A | | 11/1996 | Yoon |
| 5,573,784 A | | 11/1996 | Badylak et al. |
| 5,575,771 A | | 11/1996 | Walinsky |
| 5,584,842 A | | 12/1996 | Fogarty et al. |
| 5,584,879 A | | 12/1996 | Reimold et al. |
| 5,591,177 A | | 1/1997 | Lehrer |
| 5,591,179 A | | 1/1997 | Edelstein |
| 5,591,205 A | | 1/1997 | Fowler |
| 5,591,206 A | | 1/1997 | Moufarrege |
| 5,593,412 A | | 1/1997 | Martinez et al. |
| 5,593,421 A | | 1/1997 | Bauer |
| 5,601,602 A | | 2/1997 | Fowler |
| 5,603,718 A | | 2/1997 | Xu |

(56) References Cited

U.S. PATENT DOCUMENTS

| | | |
|---|---|---|
| 5,607,435 A | 3/1997 | Sachdeva et al. |
| 5,609,597 A * | 3/1997 | Lehrer .................. 606/139 |
| 5,611,794 A | 3/1997 | Sauer et al. |
| 5,613,974 A | 3/1997 | Andreas et al. |
| 5,613,975 A | 3/1997 | Christy |
| 5,618,291 A | 4/1997 | Thompson et al. |
| 5,620,452 A | 4/1997 | Yoon |
| 5,620,461 A | 4/1997 | Muijs et al. |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,647,372 A * | 7/1997 | Tovey et al. .................. 600/562 |
| 5,649,959 A | 7/1997 | Hannam et al. |
| D383,539 S | 9/1997 | Croley |
| 5,662,664 A | 9/1997 | Gordon et al. |
| 5,669,917 A | 9/1997 | Sauer et al. |
| 5,669,935 A | 9/1997 | Rosenman et al. |
| 5,672,174 A | 9/1997 | Gough et al. |
| 5,674,231 A | 10/1997 | Green et al. |
| 5,676,689 A | 10/1997 | Kensey et al. |
| 5,676,974 A | 10/1997 | Valdes et al. |
| 5,681,334 A | 10/1997 | Evans et al. |
| 5,683,405 A | 11/1997 | Yacoubian et al. |
| 5,690,674 A | 11/1997 | Diaz |
| 5,693,061 A * | 12/1997 | Pierce et al. .................. 606/198 |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,707,379 A | 1/1998 | Fleenor et al. |
| 5,713,899 A | 2/1998 | Marnay et al. |
| 5,713,910 A | 2/1998 | Gordon et al. |
| 5,716,369 A | 2/1998 | Riza |
| 5,716,375 A | 2/1998 | Fowler |
| 5,720,574 A | 2/1998 | Barella |
| 5,720,755 A | 2/1998 | Dakov |
| 5,720,757 A | 2/1998 | Hathaway et al. |
| 5,722,981 A | 3/1998 | Stevens |
| 5,725,498 A | 3/1998 | Janzen et al. |
| 5,725,552 A | 3/1998 | Kotula et al. |
| 5,725,554 A | 3/1998 | Simon et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,728,151 A | 3/1998 | Garrison et al. |
| 5,732,872 A | 3/1998 | Bolduc et al. |
| 5,735,736 A | 4/1998 | Volk |
| 5,735,873 A | 4/1998 | MacLean |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,749,898 A * | 5/1998 | Schulze et al. .................. 606/228 |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,759,188 A | 6/1998 | Yoon |
| 5,759,189 A * | 6/1998 | Ferragamo et al. .......... 606/148 |
| 5,766,183 A | 6/1998 | Sauer |
| 5,766,186 A | 6/1998 | Faraz et al. |
| 5,766,217 A * | 6/1998 | Christy .................. 606/148 |
| 5,766,246 A | 6/1998 | Mulhauser et al. |
| 5,769,862 A | 6/1998 | Kammerer et al. |
| 5,769,870 A | 6/1998 | Salahieh et al. |
| 5,779,707 A | 7/1998 | Bertholet et al. |
| 5,779,719 A | 7/1998 | Klein et al. |
| 5,782,844 A | 7/1998 | Yoon et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,795,958 A | 8/1998 | Rao et al. |
| 5,797,928 A | 8/1998 | Kogasaka |
| 5,797,929 A * | 8/1998 | Andreas et al. ............... 606/148 |
| 5,797,931 A | 8/1998 | Bito et al. |
| 5,797,933 A | 8/1998 | Snow et al. |
| 5,797,958 A | 8/1998 | Yoon |
| 5,799,661 A | 9/1998 | Boyd et al. |
| 5,810,776 A | 9/1998 | Bacich et al. |
| 5,810,845 A * | 9/1998 | Yoon .................. 606/139 |
| 5,810,846 A | 9/1998 | Virnich et al. |
| 5,810,849 A | 9/1998 | Kontos |
| 5,810,850 A | 9/1998 | Hathaway et al. |
| 5,810,851 A | 9/1998 | Yoon |
| 5,814,052 A | 9/1998 | Nakao et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,827,298 A | 10/1998 | Hart et al. |
| 5,830,125 A | 11/1998 | Scribner et al. |
| 5,833,698 A | 11/1998 | Hinchliffe et al. |
| 5,836,955 A | 11/1998 | Buelna et al. |
| 5,836,956 A | 11/1998 | Buelna et al. |
| 5,843,167 A | 12/1998 | Dwyer et al. |
| 5,845,657 A | 12/1998 | Carberry et al. |
| 5,846,253 A | 12/1998 | Buelna et al. |
| 5,848,714 A | 12/1998 | Robson et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,855,585 A | 1/1999 | Kontos |
| 5,858,082 A | 1/1999 | Cruz et al. |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,865,791 A | 2/1999 | Whayne et al. |
| 5,868,755 A | 2/1999 | Kanner et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,502 A | 2/1999 | Suryadevara |
| 5,871,525 A | 2/1999 | Edwards et al. |
| 5,873,876 A | 2/1999 | Christy |
| 5,876,411 A | 3/1999 | Kontos |
| 5,879,366 A | 3/1999 | Shaw et al. |
| 5,891,088 A | 4/1999 | Thompson et al. |
| 5,897,487 A * | 4/1999 | Ouchi .................. 600/127 |
| 5,897,564 A | 4/1999 | Schulze et al. |
| 5,902,310 A | 5/1999 | Foerster et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,620 A * | 5/1999 | Nakao et al. .................. 606/113 |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,921,994 A | 7/1999 | Andreas et al. |
| 5,922,009 A | 7/1999 | Epstein et al. |
| 5,928,266 A | 7/1999 | Kontos |
| 5,935,147 A | 8/1999 | Kensey et al. |
| 5,938,667 A | 8/1999 | Peyser et al. |
| 5,941,890 A | 8/1999 | Voegele et al. |
| 5,944,728 A | 8/1999 | Bates |
| 5,947,999 A | 9/1999 | Groiso |
| 5,951,518 A | 9/1999 | Licata et al. |
| 5,951,547 A | 9/1999 | Gough et al. |
| 5,951,576 A | 9/1999 | Wakabayashi |
| 5,951,589 A | 9/1999 | Epstein et al. |

(56) References Cited

U.S. PATENT DOCUMENTS

| | | |
|---|---|---|
| 5,951,590 A | 9/1999 | Goldfarb |
| 5,954,732 A | 9/1999 | Hart et al. |
| 5,957,936 A * | 9/1999 | Yoon et al. ................. 606/144 |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,009 A | 10/1999 | Fortier et al. |
| 5,972,030 A | 10/1999 | Garrison et al. |
| 5,976,161 A | 11/1999 | Kirsch et al. |
| 5,980,517 A | 11/1999 | Gough et al. |
| 5,980,539 A | 11/1999 | Kontos |
| 5,984,934 A | 11/1999 | Ashby et al. |
| 5,984,949 A | 11/1999 | Levin |
| 5,984,950 A | 11/1999 | Cragg et al. |
| 5,993,466 A | 11/1999 | Yoon |
| 5,993,468 A | 11/1999 | Rygaard |
| 5,993,476 A | 11/1999 | Groiso |
| 5,997,555 A | 12/1999 | Kontos |
| 6,001,109 A | 12/1999 | Kontos |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,022,372 A | 2/2000 | Kontos |
| 6,024,747 A | 2/2000 | Kontos |
| 6,024,750 A | 2/2000 | Mastri |
| 6,030,364 A | 2/2000 | Durgin et al. |
| 6,030,413 A | 2/2000 | Lazarus |
| 6,033,427 A | 3/2000 | Lee |
| 6,036,699 A | 3/2000 | Andreas et al. |
| 6,036,703 A | 3/2000 | Evans et al. |
| 6,036,720 A | 3/2000 | Abrams et al. |
| 6,042,601 A | 3/2000 | Smith |
| 6,045,570 A | 4/2000 | Epstein et al. |
| 6,048,351 A | 4/2000 | Gordon et al. |
| 6,048,354 A | 4/2000 | Lawrence |
| 6,048,357 A | 4/2000 | Kontos |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,719 A | 5/2000 | Yamamoto et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,068,603 A * | 5/2000 | Suzuki ................. 600/565 |
| 6,071,300 A | 6/2000 | Brenneman et al. |
| 6,077,276 A | 6/2000 | Kontos |
| 6,077,279 A | 6/2000 | Kontos |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,612 A | 9/2000 | Swanson et al. |
| 6,117,125 A | 9/2000 | Rothbarth et al. |
| 6,117,144 A | 9/2000 | Nobles et al. |
| 6,117,145 A | 9/2000 | Wood et al. |
| 6,117,148 A | 9/2000 | Ravo |
| 6,117,157 A | 9/2000 | Tekulve |
| 6,120,513 A | 9/2000 | Bailey et al. |
| 6,120,524 A | 9/2000 | Taheri |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,143,004 A | 11/2000 | Davis et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,178,355 B1 | 1/2001 | Williams et al. |
| 6,190,396 B1 | 2/2001 | Whitin et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,206,893 B1 | 3/2001 | Klein et al. |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 * | 4/2001 | Fleenor ................. 606/148 |
| 6,221,102 B1 | 4/2001 | Baker et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,305,891 B1 | 10/2001 | Burlingame |
| 6,306,081 B1 * | 10/2001 | Ishikawa et al. ............. 600/127 |
| 6,315,782 B1 * | 11/2001 | Chu et al. ................. 606/113 |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,059 B1 | 2/2002 | Hathaway et al. |
| 6,348,064 B1 | 2/2002 | Kanner |
| 6,355,050 B1 | 3/2002 | Andreas et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,428,549 B1 | 8/2002 | Kontos |
| 6,436,109 B1 | 8/2002 | Kontos |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,451,031 B1 | 9/2002 | Kontos |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,209 B2 | 1/2003 | Ouchi |
| 6,506,210 B1 | 1/2003 | Kanner |
| 6,508,828 B1 | 1/2003 | Akerfeldt et al. |
| 6,511,489 B2 | 1/2003 | Field et al. |
| 6,517,498 B1 | 2/2003 | Burbank et al. |
| 6,517,553 B2 | 2/2003 | Klein et al. |

(56) References Cited

U.S. PATENT DOCUMENTS

| | | | |
|---|---|---|---|
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 * | 6/2003 | Kalloo et al. | 606/151 |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,623,509 B2 | 9/2003 | Ginn |
| 6,623,510 B2 | 9/2003 | Carly et al. |
| 6,626,918 B1 | 9/2003 | Ginn et al. |
| 6,632,237 B2 | 10/2003 | Ben-David et al. |
| 6,632,238 B2 | 10/2003 | Ginn et al. |
| 6,634,537 B2 | 10/2003 | Chen |
| 6,641,592 B1 | 11/2003 | Sauer et al. |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,051 B2 * | 2/2004 | Nakada et al. | 600/140 |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,716,228 B2 | 4/2004 | Tal |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 * | 6/2004 | Dana et al. | 606/148 |
| 6,749,621 B2 | 6/2004 | Pantages et al. |
| 6,749,622 B2 | 6/2004 | McGuckin, Jr. et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,911,034 B2 | 6/2005 | Nobles et al. |
| 6,926,723 B1 | 8/2005 | Mulhauser et al. |
| 6,926,731 B2 | 8/2005 | Coleman et al. |
| 6,939,357 B2 | 9/2005 | Navarro et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,029,480 B2 | 4/2006 | Klein et al. |
| 7,029,481 B1 | 4/2006 | Burdulis, Jr. et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 * | 6/2006 | Okada | 600/127 |
| 7,063,710 B2 | 6/2006 | Takamoto et al. |
| 7,063,711 B1 | 6/2006 | Loshakove et al. |
| 7,083,635 B2 | 8/2006 | Ginn |
| 7,108,709 B2 | 9/2006 | Cummins |
| 7,111,768 B2 | 9/2006 | Cummins et al. |
| 7,112,225 B2 | 9/2006 | Ginn |
| 7,122,002 B2 * | 10/2006 | Okada | 600/127 |
| 7,144,411 B2 | 12/2006 | Ginn et al. |
| 7,147,646 B2 * | 12/2006 | Dana et al. | 606/148 |
| 7,160,309 B2 | 1/2007 | Voss |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,179,266 B2 | 2/2007 | Kontos |
| 7,211,101 B2 | 5/2007 | Carley et al. |
| 7,229,458 B2 | 6/2007 | Boecker et al. |
| 7,235,087 B2 | 6/2007 | Modesitt et al. |
| 7,270,672 B1 * | 9/2007 | Singer | 606/148 |
| 7,311,720 B2 | 12/2007 | Mueller et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,338,514 B2 | 3/2008 | Wahr et al. |
| D566,272 S | 4/2008 | Walburg et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,396,359 B1 | 7/2008 | Derowe et al. |
| 7,431,727 B2 | 10/2008 | Cole et al. |
| 7,445,626 B2 | 11/2008 | Songer et al. |
| 7,449,024 B2 | 11/2008 | Stafford |
| 7,462,188 B2 | 12/2008 | McIntosh |
| 7,507,200 B2 * | 3/2009 | Okada | 600/104 |
| 7,533,790 B1 | 5/2009 | Knodel et al. |
| 7,588,580 B2 * | 9/2009 | Okada | A61B 1/00087 600/104 |
| 7,597,706 B2 | 10/2009 | Kanner et al. |
| 7,645,285 B2 | 1/2010 | Cosgrove et al. |
| 7,648,493 B2 | 1/2010 | Forsberg et al. |
| D611,144 S | 3/2010 | Reynolds |
| 7,727,249 B2 * | 6/2010 | Rahmani | 606/170 |
| 7,731,655 B2 | 6/2010 | Smith et al. |
| 7,749,249 B2 | 7/2010 | Gelbart et al. |
| 7,799,042 B2 | 9/2010 | Williamson, IV et al. |
| 7,901,428 B2 | 3/2011 | Ginn et al. |
| 8,007,504 B2 * | 8/2011 | Zenati et al. | 606/151 |
| 8,226,666 B2 | 7/2012 | Zarbatany et al. |
| 8,313,497 B2 | 11/2012 | Walberg et al. |
| 8,469,969 B2 | 6/2013 | Kear et al. |
| 8,480,687 B2 | 7/2013 | Ducharme et al. |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2001/0053909 A1 * | 12/2001 | Nakada et al. | 606/47 |
| 2002/0026215 A1 | 2/2002 | Redmond et al. |
| 2002/0038127 A1 | 3/2002 | Blatter et al. |
| 2002/0042622 A1 | 4/2002 | Vargas et al. |

(56) References Cited

U.S. PATENT DOCUMENTS

| | | |
|---|---|---|
| 2002/0045908 A1 | 4/2002 | Nobles et al. |
| 2002/0049427 A1 | 4/2002 | Wiener et al. |
| 2002/0058960 A1 | 5/2002 | Hudson et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0177876 A1 | 11/2002 | Roby et al. |
| 2002/0183786 A1 | 12/2002 | Girton |
| 2002/0188275 A1 | 12/2002 | McGuckin, Jr. |
| 2003/0004543 A1 | 1/2003 | Gleeson et al. |
| 2003/0009180 A1 | 1/2003 | Hinchliffe et al. |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093093 A1 | 5/2003 | Modesitt et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0158577 A1 | 8/2003 | Pantages et al. |
| 2003/0158578 A1 | 8/2003 | Pantages et al. |
| 2003/0187457 A1 | 10/2003 | Weber |
| 2003/0195504 A1 | 10/2003 | Tallarida et al. |
| 2003/0195529 A1 | 10/2003 | Takamoto et al. |
| 2003/0195561 A1 | 10/2003 | Carley et al. |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0092968 A1 | 5/2004 | Caro et al. |
| 2004/0093027 A1 | 5/2004 | Fabisiak et al. |
| 2004/0097978 A1 | 5/2004 | Modesitt et al. |
| 2004/0098044 A1 | 5/2004 | Van de Moer et al. |
| 2004/0116943 A1* | 6/2004 | Brandt et al. .............. 606/144 |
| 2004/0122349 A1 | 6/2004 | Lafontaine et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1* | 8/2004 | Okada .............. 600/127 |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0210251 A1 | 10/2004 | Kontos |
| 2004/0215232 A1 | 10/2004 | Belhe et al. |
| 2004/0225194 A1 | 11/2004 | Smith et al. |
| 2004/0225301 A1 | 11/2004 | Roop et al. |
| 2004/0236354 A1 | 11/2004 | Seguin |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0010248 A1 | 1/2005 | Lafontaine |
| 2005/0033359 A1 | 2/2005 | Dycus |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0143761 A1 | 6/2005 | Modesitt et al. |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0187564 A1 | 8/2005 | Jayaraman |
| 2005/0216057 A1 | 9/2005 | Coleman et al. |
| 2005/0222614 A1 | 10/2005 | Ginn et al. |
| 2005/0234396 A1 | 10/2005 | Forsberg et al. |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0261708 A1 | 11/2005 | Pasricha et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0079914 A1 | 4/2006 | Modesitt et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0106420 A1 | 5/2006 | Dolan et al. |
| 2006/0135989 A1 | 6/2006 | Carley et al. |
| 2006/0142785 A1 | 6/2006 | Modesitt et al. |
| 2006/0144479 A1 | 7/2006 | Carley et al. |
| 2006/0167477 A1 | 7/2006 | Arcia et al. |
| 2006/0167484 A1 | 7/2006 | Carley et al. |
| 2006/0173469 A1 | 8/2006 | Klein |
| 2006/0190014 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0287674 A1 | 12/2006 | Ginn et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0032798 A1 | 2/2007 | Pantages et al. |
| 2007/0032799 A1 | 2/2007 | Pantages et al. |
| 2007/0032801 A1 | 2/2007 | Pantages et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083230 A1 | 4/2007 | Javois |
| 2007/0083231 A1 | 4/2007 | Lee |
| 2007/0112304 A1 | 5/2007 | Voss |
| 2007/0123817 A1 | 5/2007 | Khosravi et al. |
| 2007/0123936 A1 | 5/2007 | Goldin et al. |
| 2007/0167959 A1 | 7/2007 | Modesitt et al. |
| 2007/0179527 A1 | 8/2007 | Eskuri et al. |
| 2007/0198058 A1 | 8/2007 | Gelbart et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |

(56) References Cited

U.S. PATENT DOCUMENTS

| | | |
|---|---|---|
| 2007/0265658 A1 | 11/2007 | Nelson et al. |
| 2007/0270904 A1 | 11/2007 | Ginn |
| 2007/0276410 A1 | 11/2007 | McIntosh |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282354 A1 | 12/2007 | McIntosh |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0114395 A1 | 5/2008 | Mathisen et al. |
| 2008/0210737 A1 | 9/2008 | Ginn et al. |
| 2008/0221616 A1 | 9/2008 | Ginn et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1 | 11/2008 | Andreas et al. |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319458 A1 | 12/2008 | Reynolds |
| 2008/0319475 A1 | 12/2008 | Clark |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0088779 A1 | 4/2009 | Zung et al. |
| 2009/0088794 A1 | 4/2009 | LaFontaine |
| 2009/0105728 A1 | 4/2009 | Noda et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0157105 A1 | 6/2009 | Zung et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0306681 A1 | 12/2009 | Del Nido et al. |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0234884 A1 | 9/2010 | Lafontaine et al. |
| 2011/0066163 A1 | 3/2011 | Cho et al. |
| 2012/0245603 A1 | 9/2012 | Voss |
| 2012/0296374 A1 | 11/2012 | Ziobro et al. |

FOREIGN PATENT DOCUMENTS

| | | |
|---|---|---|
| DE | 4210724 | 7/1993 |
| DE | 9217932 | 7/1993 |
| DE | 4220283 | 12/1993 |
| DE | 197 11 288 | 10/1998 |
| DE | 29723736 U1 | 4/1999 |
| DE | 19859952 | 2/2000 |
| DE | 10211360 | 10/2003 |
| DE | 102006056283 | 6/2008 |
| EP | 0 140 557 | 5/1985 |
| EP | 0 207 545 | 1/1987 |
| EP | 0 386 361 | 9/1990 |
| EP | 0 474 887 | 3/1992 |
| EP | 0 478 358 | 4/1992 |
| EP | 0 478 887 | 4/1992 |
| EP | 0 543 499 | 10/1992 |
| EP | 0 534 696 | 3/1993 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 756 851 | 2/1997 |
| EP | 0 774 237 | 5/1997 |
| EP | 0 812 571 | 12/1997 |
| EP | 0 941 698 | 12/1997 |
| EP | 0 858 776 | 8/1998 |
| EP | 0 941 697 | 9/1999 |
| EP | 1 867 287 | 12/2007 |
| FR | 1059544 | 3/1954 |
| FR | 2 443 238 | 7/1980 |
| FR | 2 715 290 | 7/1995 |
| FR | 2 722 975 | 2/1996 |
| FR | 2 768 324 | 3/1999 |
| FR | 2768324 | 3/1999 |
| GB | 1 358 466 | 7/1974 |
| GB | 2 075 144 | 11/1981 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 51143386 | 11/1976 |
| JP | 5220794 | 2/1977 |
| JP | 58-181006 | 12/1983 |
| JP | 12 74750 | 11/1989 |
| JP | 2119866 | 5/1990 |
| JP | 542161 | 2/1993 |
| JP | 11500642 | 8/1997 |
| JP | 2000014634 | 1/2000 |
| JP | 2000102546 | 4/2000 |
| JP | 2005218868 A | 8/2005 |
| NL | 9302140 | 7/1995 |
| PL | 171425 | 4/1997 |
| RU | 2086192 | 8/1997 |
| SU | 495067 | 12/1975 |
| SU | 820810 | 4/1981 |
| SU | 912155 | 3/1982 |
| SU | 993922 | 2/1983 |
| SU | 1093329 | 5/1984 |
| SU | 1174036 | 8/1985 |
| SU | 1243708 | 7/1986 |
| SU | 1324650 | 7/1987 |
| SU | 1405828 | 6/1988 |
| SU | 1456109 | 2/1989 |
| SU | 1544383 | 2/1990 |
| SU | 1560133 | 4/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |

(56) References Cited

FOREIGN PATENT DOCUMENTS

| | | |
|---|---|---|
| WO | WO 96/24291 | 8/1996 |
| WO | WO 96/40356 | 12/1996 |
| WO | WO 97/00046 | 1/1997 |
| WO | WO 97/03613 | 2/1997 |
| WO | WO 97/07741 | 3/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/42262 | 10/1998 |
| WO | WO 98/58591 | 12/1998 |
| WO | WO 99/21491 | 5/1999 |
| WO | WO 99/40849 | 8/1999 |
| WO | WO 99/47049 | 9/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/12013 | 3/2000 |
| WO | WO 00/27311 | 5/2000 |
| WO | WO 00/27313 | 5/2000 |
| WO | WO 00/51498 | 9/2000 |
| WO | WO 00/56223 | 9/2000 |
| WO | WO 00/56226 | 9/2000 |
| WO | WO 00/56227 | 9/2000 |
| WO | WO 00/56228 | 9/2000 |
| WO | WO 00/69342 | 11/2000 |
| WO | WO 00/71032 | 11/2000 |
| WO | WO 01/19259 | 3/2001 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/36021 | 5/2002 |
| WO | WO 02/38055 | 5/2002 |
| WO | WO 02/45593 | 6/2002 |
| WO | WO 02/45594 | 6/2002 |
| WO | WO02/062234 | 8/2002 |
| WO | WO 02062234 | 8/2002 |
| WO | WO 02/098302 | 12/2002 |
| WO | WO 03/003925 | 1/2003 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO03/094748 | 11/2003 |
| WO | WO 03094748 | 11/2003 |
| WO | WO 03/99134 | 12/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/006990 | 1/2005 |
| WO | WO2005000126 | 1/2005 |
| WO | WO 2005000126 | 1/2005 |
| WO | WO 2005/023119 | 3/2005 |
| WO | WO 2005/025430 | 3/2005 |
| WO | WO 2005/030060 | 4/2005 |
| WO | WO2005/041782 | 5/2005 |
| WO | WO 2005041782 | 5/2005 |
| WO | WO2005/063129 | 7/2005 |
| WO | WO 2005/065549 | 7/2005 |
| WO | WO 2005063129 | 7/2005 |
| WO | WO 2005/082256 | 9/2005 |
| WO | WO 2005/092204 | 10/2005 |
| WO | WO2005/092204 | 10/2005 |
| WO | WO 2005/110240 | 11/2005 |
| WO | WO2005/112782 | 12/2005 |
| WO | WO 2005/115251 | 12/2005 |
| WO | WO 2005/115521 | 12/2005 |
| WO | WO 2005112782 | 12/2005 |
| WO | WO 2006/000514 | 1/2006 |
| WO | WO2006/026116 | 3/2006 |
| WO | WO 2006026116 | 3/2006 |
| WO | WO2006/052611 | 5/2006 |
| WO | WO2006/052612 | 5/2006 |
| WO | WO 2006052611 | 5/2006 |
| WO | WO 2006052612 | 5/2006 |
| WO | WO2006/078578 | 7/2006 |
| WO | WO 2006078578 | 7/2006 |
| WO | WO 2006/083889 | 8/2006 |
| WO | WO2006/115901 | 11/2006 |
| WO | WO2006/115904 | 11/2006 |
| WO | WO2006/118877 | 11/2006 |
| WO | WO 2006115901 | 11/2006 |
| WO | WO 2006115904 | 11/2006 |
| WO | WO 2006118877 | 11/2006 |
| WO | WO 2007/005585 | 1/2007 |
| WO | WO 2007/019016 | 2/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 60/506,536, filed Sep. 26, 2003, McIntosh.
U.S. Appl. No. 60/540,811, filed Jan. 30, 2004, McIntosh.
U.S. Appl. No. 12/365,397, filed Feb. 4, 2009, Sibbitt, Jr. et al.
U.S. Appl. No. 12/559,377, filed Sep. 14, 2009, Sibbitt, Jr. et al.
Elgin National Watch Company, Product Brochure entitled "Elgiloy. RTM., A Cobalt Nickel Spring Alloy," 33 pages.
Faulkner, Catherine B., Letter regarding "VasoSeal Vascular Hemostasis," Datascope, New Jersey, 1 page only.
International Search Report for PCT/US06/33033 dated Sep. 28, 2007.
International Search Report for PCT/US06/33031 dated May 19, 2008.
International Search Report for PCT/US06/33032 dated Sep. 27, 2007.
Laurus Medical Corporation, "Endoscopic Suturing Made Simple," The Laurus ND-2600 Needle Driver, Irvine, CA., 1 page.
Marshall, A.C. & Lock, J.E.; "Structural and compliant anatomy of the patient foramen ovale in patients undergoing transcatheter closure", Am. Heart Journ., 140(2):303-307 (2000).
Product Brochure, Laurus Medical Corporation, Irvine, CA "The Laurus In-Line Endoscopic Suturing Device" (Oct. 1994) 1 page.

(56) References Cited

OTHER PUBLICATIONS

Rema-Medizintechnik GmbH, Product Brochure entitled "REMA," 7 pages.
Taber's Cyclopedic Medical Dictionary, 18th Ed., p. 747 (1997).
U.S. Appl. No. 09/262,402, Mar. 29, 2000, Restriction Requirement.
U.S. Appl. No. 09/262,402, May 30, 2000, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 10/152,272, Jan. 24, 2005, Office Action.
U.S. Appl. No. 10/152,272, May 13, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/335,147, Dec. 20, 2006, Issue Notification.
U.S. Appl. No. 10/357,984, Jan. 9, 2006, Restriction Requirement.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/652,182, Jun. 8, 2007, Issue Notification.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/948,445, Jul. 11, 2007, Office Action.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/508,656, Dec. 9, 2009, Restriction Requirement.
U.S. Appl. No. 11/508,662, Dec. 28, 2009, Restriction Requirement.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/508,656, Aug. 30, 2010, Office Action.
U.S. Appl. No. 11/675,462, Aug. 31, 2010, Office Action.
U.S. Appl. No. 11/958,281, Sep. 2, 2010, Office Action.
U.S. Appl. No. 12/257,127, Aug. 30, 2010, Office Action.
U.S. Appl. No. 10/616,832, Sep. 20, 2010, Notice of Allowance.
U.S. Appl. No. 11/152,562, Sep. 16, 2010, Notice of Allowance.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt, Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 60/946,063, filed Jun. 25, 2007, Reynolds.
US 5,820,544, 06/1974, Semm (withdrawn).
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, the Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, A Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar.

(56) References Cited

OTHER PUBLICATIONS 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive. org, Jun. 1998, Original Publisher: http://prostar.com, may also be found at http://web.archive.org/web/19980630040429/www. perclose.com/html/prstrxl.html.

Sa Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/ productdetail by examiner on Oct. 9, 2007, publication date unavailable.

Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

Cardiac Catheterization and Angiography, 3rd Ed., Lea N ad Febiger, Philadelphia, 1986. Elgiloy Brochure, Jun. 23, 1959, Elgin National Watch Co., Elgin, IL.

Cardio-Thoracic Systems Prospectus dated Mar. 20, 1996.

Datascope Corporation, Montvale, NJ (1991) 1 PG, American Heart Assoc. Meeting, Anaheim.

Kensey Nash Corporation, Exton, PA, "The Hemostatic Puncture Closure Device", 2 pages.

Nakamura, S. et al., Techniques for Palmaz-Schatz Stent Deployment in Lesions With a Large Side Branch, Catheterization and Cardiovascular Diagnosis, 34: 353-361, 1995.

Product Brochure, "SuperStitch—Closure Made SimpleTM", Sutura, Inc. (2003).

Serruys, PW et al., A Comparision of Balloon-Expandable-Stent lmplantaion With Balloon Angioplasty in Patients With Coronary Artery Disease, New England Journal of Medicine, 331:489-495,1994.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.

(56) References Cited

OTHER PUBLICATIONS

U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Office Action.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.

(56) References Cited

OTHER PUBLICATIONS

U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999 Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.

(56) References Cited

OTHER PUBLICATIONS

U.S. Appl. No. 09/988,541, Dec. 13, 2005, Notice of Allowance.
U.S. Appl. No. 10/033,689, Sep. 30, 2003, Office Action.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/660,288, Mar. 30, 2010, Office Action.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/877,974, Jul. 9, 2008, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 2, 2010, Office Action.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/552,593, Mar. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,513, Apr. 9, 2010, Office Action.
U.S. Appl. No. 90/006,469, Nov. 29, 2002, Request for Re-Examination.
U.S. Appl. No. 90/006,469, Sep. 10, 2004, Re-examination Office Action.
U.S. Appl. No. 90/006,469, Sep. 27, 2005, Notice of Intent.
U.S. Appl. No. 90/006,469, Jun. 27, 2006, Re-examination Certification.
U.S. Appl. No. 12/365,397, Sep. 13, 2010, Office Action.
U.S. Appl. No. 11/891,513, Sep. 28, 2010, Office Action.
U.S. Appl. No. 10/787073, Sep. 15, 2010, Issue Notification.
U.S. Appl. No. 11/767,818, Sep. 30, 2010, Office Action.
U.S. Appl. No. 12/365,397, Jun. 21, 2011, Notice of Allowance.
U.S. Appl. No. 12/365,397, Oct. 12, 2011, Issue Notification.
U.S. Appl. No. 12/559,377, Feb. 27, 2012, Office Action.
U.S. Appl. No. 12/559,377, Dec. 14, 2011, Restriction Requirement.
U.S. Appl. No. 12/559,377, Aug. 3, 2012, Office Action.
U.S. Appl. No. 11/508,662, Oct. 26, 2010, Office Action.
U.S. Appl. No. 12/365,397, Dec. 17, 2010, Office Action.
U.S. Appl. No. 11/508,656, Feb. 10, 2014, Notice of Allowance.
U.S. Appl. No. 11/508,656, Jun. 4, 2014, Issue Notification.
U.S. Appl. No. 11/508,662, Mar. 24, 2014, Office Action.
U.S. Appl. No. 13/052,634, Feb. 8, 2013, Restriction Requirement.
U.S. Appl. No. 13/052,634, Apr. 22, 2013, Office Action.
U.S. Appl. No. 13/052,634, Nov. 8, 2013, Office Acton.
U.S. Appl. No. 13/111,403, Jun. 28, 2013, Restriction Requirement.
U.S. Appl. No. 13/111,403, Sep. 5, 2013, Office Action.
U.S. Appl. No. 13/111,403, Dec. 24, 2013, Office Action.
U.S. Appl. No. 14/532,537, Nov. 4, 2014, Sibbitt, Jr. et al.
U.S. Appl. No. 11/508,662, Jul. 25, 2014, Notice of Allowance.
U.S. Appl. No. 12/559,377, Jul. 30, 2014, Notice of Allowance.
U.S. Appl. No. 13/111,403, Nov. 20, 2014, Office Action.
U.S. Appl. No. 13/052,634, Dec. 24, 2014, Office Action.
U.S. Appl. No. 13/052,634, Jun. 3, 2015, Notice of Allowance.
U.S. Appl. No. 13/111,403, May 7, 2015, Office Action.
U.S. Appl. No. 13/111,403, Oct. 7, 2015, Office Action.

* cited by examiner

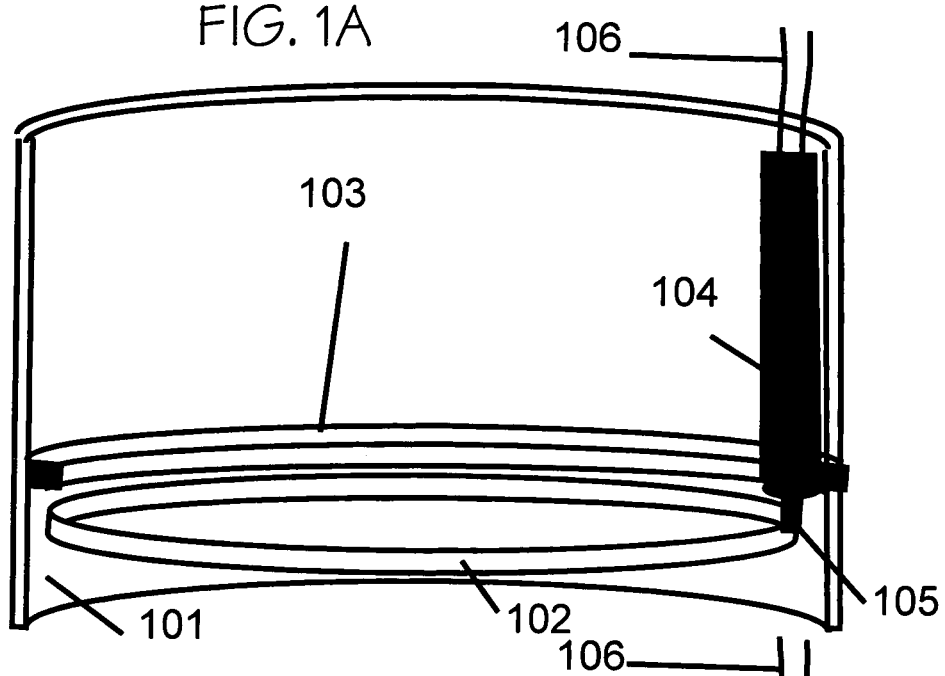
FIG. 1A
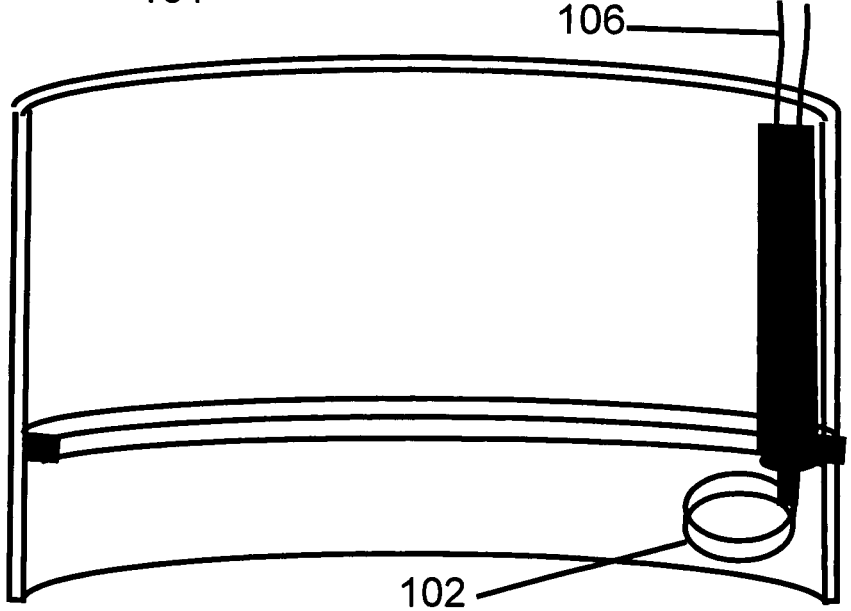
FIG. 1B
FIG. 1

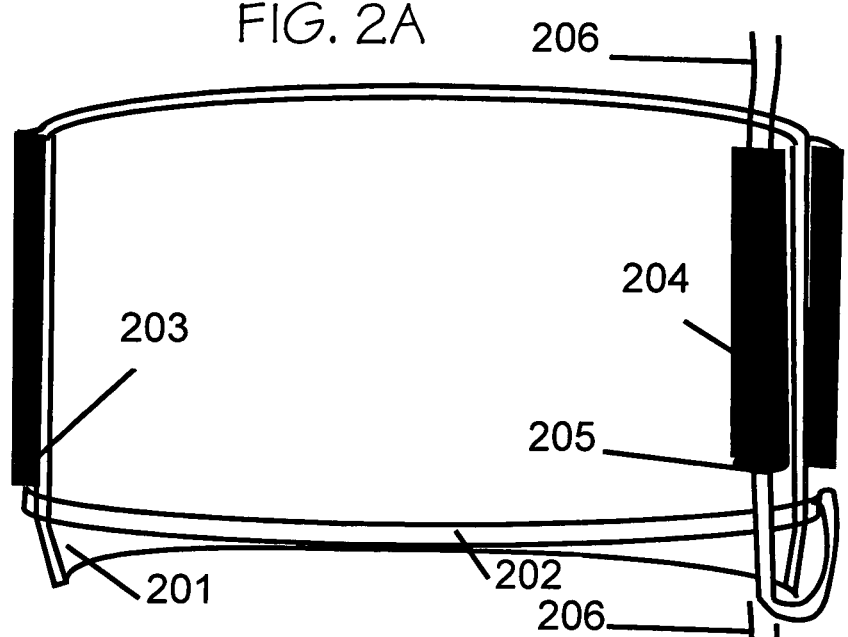
FIG. 2A
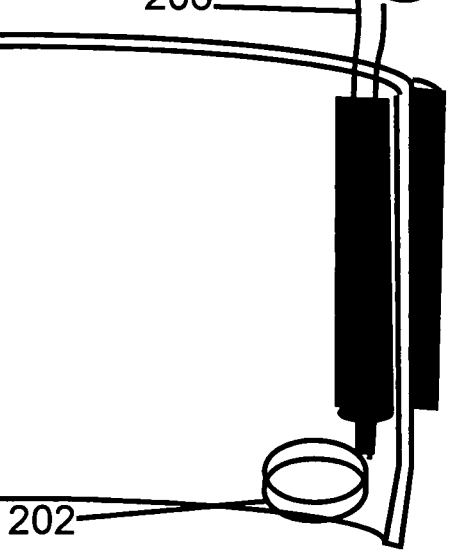
FIG. 2B
FIG. 2

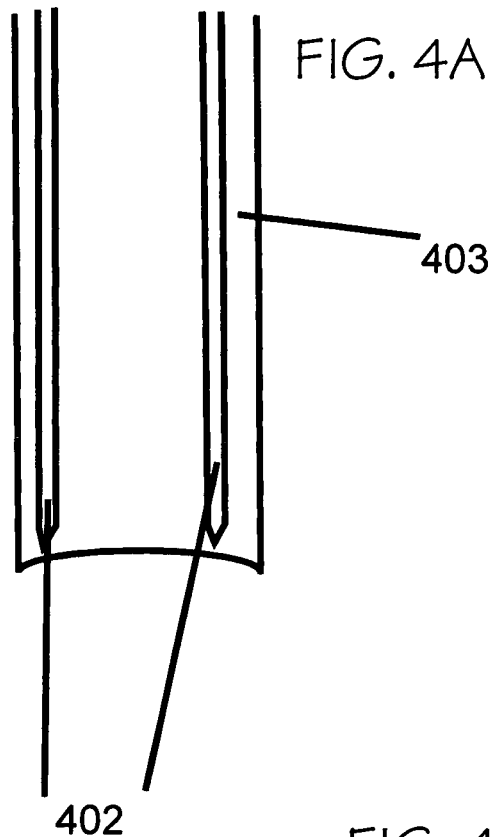
FIG. 4A
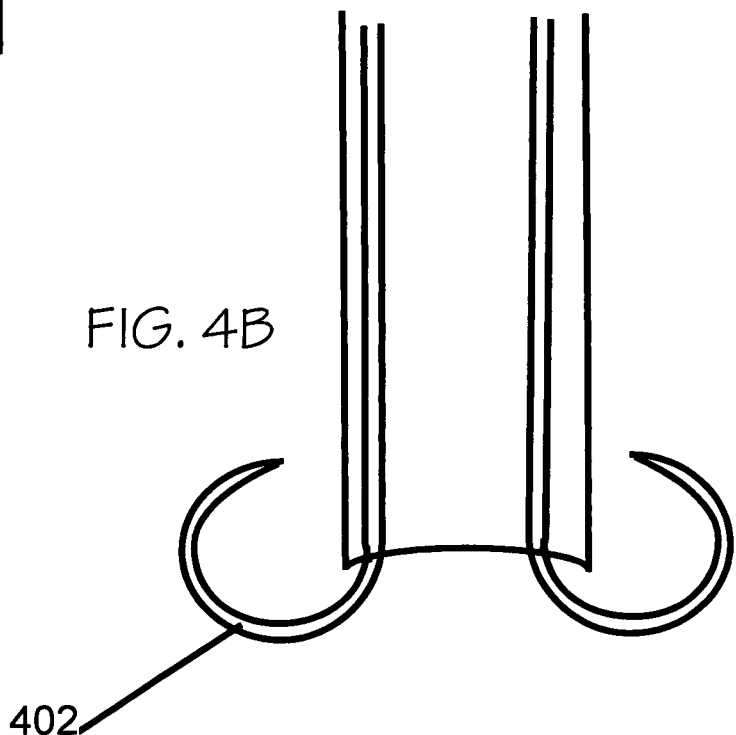
FIG. 4B
FIG. 4

VASCULAR CLOSURE METHODS AND APPARATUSES

CROSS-REFERENCE TO RELATED APPLICATIONS

This application claims priority to U.S. provisional application 60/711,279, filed Aug. 24, 2005, and is a continuation-in-part of U.S. utility application Ser. No. 11/316,775, filed Dec. 23, 2005 now abandoned, each of which is incorporated herein by reference.

FIELD OF THE INVENTION

The present invention relates to methods and apparatuses for closing punctures and apertures in human and animal tissue and to methods and apparatuses for inserting such an apparatus into such tissue to perform such closure functions.

BACKGROUND

This application is related to U.S. provisional application 60/711,279, filed Aug. 25, 2005, and U.S. utility application Ser. No. 11/316,775, filed Dec. 23, 2005, each of which is incorporated herein by reference. During angiography and related procedures, catheters are inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, plaque removal, and infusion of a therapeutic substance. After the procedure is completed and the catheter is removed from the patient, the access hole must be closed to prevent massive hemorrhage. This is conventionally achieved by applying pressure over the blood vessel manually and then by applying a pressure bandage, compressive weight, or clamp device. With conventional methods, the rate of post-puncture hemorrhage is high, which causes considerable complications. This complication is exacerbated by the concomitant use of anticoagulant medications such as heparin or warfarin and by antiplatelet drugs, which are commonly used to treat vascular disease.

Sutures have been used to close access puncture wounds in blood vessels. For example, U.S. Pat. No. 5,613,974 describes a device and method for applying sutures to a vascular puncture, U.S. Pat. Pub. 2004/0093027A1 describes barbed suture-like material that apposes the puncture site, while U.S. Pat. Pub. 2005/0121042 A1 describes a device and method for applying suture to a vascular puncture. Difficulties with these methods include the large number of steps necessary to deploy the needles, capture the suture, withdraw the suture, tie the knot, and cut the suture. In addition, the hole in the blood vessel is often widened by insertion of the instrument, and the suture remains intravascularly on the endothelial surface, and thus can be a nidus for thrombus or intravascular mural hyperplasia with later spontaneous and catastrophic closure of the vessel.

Extravascular plugs have also been proposed for closure of vascular punctures. For example, U.S. Pat. Nos. 5,254,105 and 5,330,445 describe an extravascular plug which is slid down the external surface of the catheter or introducer and is placed into the puncture site in this manner. U.S. Pat. No. 5,643,318 relates to a similar device that has its own vessel locator device, while U.S. Pat. Pubs. 20020022822A1 and 2004/0158287A1 describe an extravascular plug that is delivered with a specialized system, U.S. Pat. Pub. 20040215232A1 describes an extravascular plug with an intravascular anchor set with a sheath with a detection port, and U.S. Pat. Pub. 2005/0085855A1 describes an extravascular collagen plug, held in place with an intravascular anchor, and a device that locks over a piece of suture. Other extravascular plugs are described in U.S. Pat. No. 5,906,631, which describes a plug made of hydrophilic material, U.S. Pat. No. 6,126,675 which describes an intravascular anchor and a bioabsorble extravascular plug, U.S. Pat. No. 6,623,509 which describes a bioabsorbable plug, U.S. Pat. No. 6,569,185 which describes an injectable vascular plug, and U.S. Pat. No. 6,663,655 which describes a plug that screws in the puncture tract. U.S. Pat. Nos. 6,296,657 and 6,743,195 describe an inflatable balloon that puts pressure on the puncture site, while U.S. Pat. Pub. 2004/0143290 A1 describes a combination of an intraluminal balloon and injectable sealant. Disadvantages to these methods are related to the high likelihood of thrombosis associated with the intravascular plug or anchor, and the presence of collagen or other bioabsorble materials which cause inflammation, activate the clotting cascade, and increase the likelihood of thrombosis, which, in an arterial system, is catastrophic.

Vascular patches have also been used for repairing blood vessels, but usually only for large areas of damage. For example, U.S. Pat. No. 5,100,422 describes a vascular patch that is sutured to the external surface of the damaged blood vessel and U.S. Pat. No. 5,100,422 describes a vascular patch achieved by instilled adhesives and the device for doing such; however, these are generally impractical for catheter-based methods. U.S. Pat. Nos. 6,248,124 and 5,507,744 describe devices and methods that use electrocautery for sealing vascular punctures, but this also requires a complicated device, and perforation and thrombosis are very real possibilities.

Vascular clips or staples delivered through a catheter device have also been proposed. These devices have penetrating members that bring the edges of the tissue together. For example, U.S. Pat. No. 6,695,867 describes a clip or staple that is delivered by a specialized device, U.S. Pat. No. 6,749,622 describes a number of different clips with sharpened barbs or ends that include both intra- and extravascular portions, made of metal with memory characteristics, U.S. Pat. No. 5,861,005 describes an arterial staple that is delivered with a specialized device, U.S. Pat. Nos. 6,296,657, 6,663,655, and 6,749,621 describe a clip that is external to the vessel, but clips the two sides of the puncture together, and a device for achieving such, while U.S. Pat. Nos. 5,782,861 and 5,964,782 describe clip devices composed of two or more prongs or hooks that, depending on the direction of the prongs, can clip together the puncture site from the intra- or extravascular position, through the use of a collar which forces the prongs together or other mechanisms. U.S. Pat. No. 5,919,207 describes a stapling system based on long hooked wires that appose the surfaces, with a small staple gun to close the lesion, while U.S. Pat. No. 6,022,372 describes a similar staple gun. These clip devices are composed of thick semi-rigid material, and can be placed only with a specialized instruments, and because of the rigidity have great potential to injure or cut the blood vessel. Disadvantages of these clip devices in general include difficulty in retrieving the device if misplaced, excessive manipulation required, the thickness of the clip material which tends to cut or shear the blood vessel, the large forces that must be used to curve the staples and fix the clips, the increased possibility of tearing the blood vessel, and the general lack of control of the forces being applied to the blood vessel.

Accordingly, there is a need for methods and apparatuses that are suitable for closure of vascular punctures or other openings, and that do not suffer from the drawbacks of conventional approaches.

SUMMARY OF THE INVENTION

The present invention provides methods and apparatuses that are suitable for closure of vascular punctures or other openings, and that do not suffer from the drawbacks of conventional approaches.

The present invention comprises a tissue closure device, comprised of a cincture, noose, or snare of suture or other material, which can be tightened over a puncture wound, closing the wound from the external surface of this wound.

The present invention also comprises methods for closing tissue openings, comprising a) passing a device while in a first compressed condition through a sheath that penetrates the proximal surface of the tissue; b) extruding the device from the sheath into space beyond the proximal surface of the tissue such that the device assumes an expanded configuration; c) manipulating the device such that tissue engagement elements of the device engage the tissue; d) putting traction on the device, everting the edges of the opening, e) placing another sheath over the device, which sheath contains a cincture or noose which when dislodged or tightened from the sheath first engages, and then closes the opening by closing the cincture, h) removing the traction device and overlying sheaths, resulting in a cincture closure of the wound. The sheath can comprise various shapes and materials, as examples a solid walled or porous walled cylinder or other shape, or a plurality of guide rods or bars mounted relative to each other.

The present invention can provide a cincture or noose-like device comprising fine, strong, flexible material that after delivery ties off or closes a puncture wound. The device can be viewed as analogous in structure and design as a snare, noose, or cincture, and is similar in design to closure methods used for sacks and garbage bags. As a catheter is withdrawn from an opening, a traction or gripping device can be pulled against the interior of a blood vessel (or other tissue having an opening to be closed) and hooks or grasping features that are part of the traction or gripping device seize and/or penetrate the interior of the vessel wall. The traction or gripping device can be adapted to apply minimal shear force to the vessel wall, for example by forming the device with a plurality of flexible the members with minimal cutting surfaces. A larger sheath containing a cincture can be placed over the traction sheath, and while placing traction on the gripping members, the cincture can be closed about the everted wound edges, closing the wound. The traction device can be removed, resulting in complete closure of the puncture wound. If there is no blood leakage through the closure and the cincture device is properly positioned and stable, then the guidewire can be removed and the retaining suture or string loop cut, resulting is complete and rapid closure, which can then heal. Alternatively, the guidewire can be removed first, and the traction device removed last.

Since the present invention brings the puncture edges together and the cincture remains on the external surface of the blood vessel, there is true blood vessel healing with little endothelial disruption, reducing the chances of thrombosis or intimal hyperplasia. The device can be supplied in different diameters (e.g., french) to accommodate different sizes of catheters and different sizes of puncture holes.

BRIEF DESCRIPTION OF THE FIGURES

The invention is explained by using embodiment examples and corresponding drawings, which are incorporated into and form part of the specification.

FIG. 1(a,b) is a schematic illustration of a vascular closure device according to the present invention.

FIG. 2(a,b) is a schematic illustration of a vascular closure device according to the present invention.

FIG. 4(a,b) is a schematic illustration of a gripper and sheath according to the present invention.

DETAILED DESCRIPTION

Figure 3A:
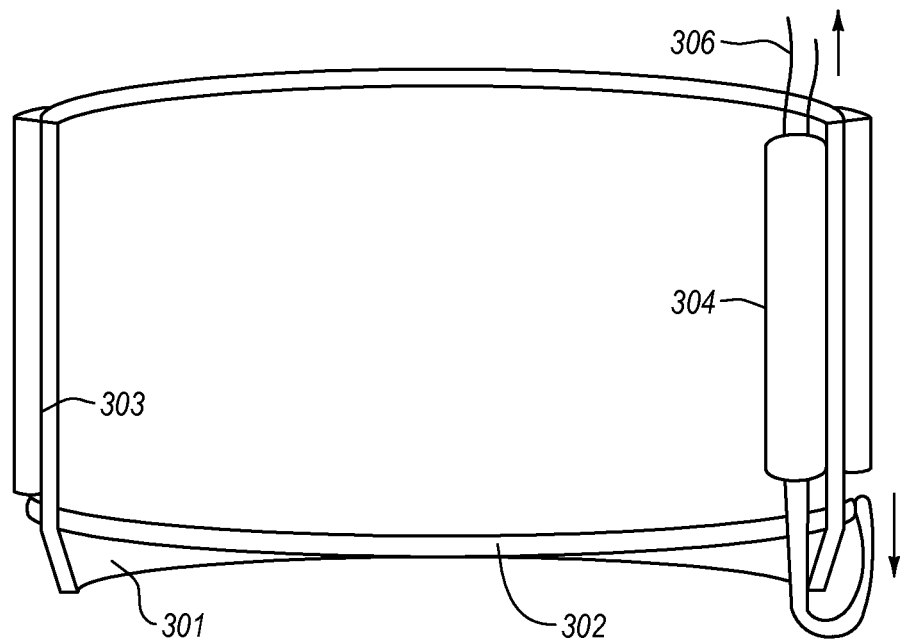
FIG. 3(a,b) is a schematic illustration of a vascular closure device according to the present invention.

The present invention provides apparatuses and methods for closing a vascular puncture wound or any tissue aperture, for example those resulting from the insertion of a vascular catheter or surgical instrument, trauma or disease. The present invention embraces both apparatus and method aspects of devices for closing a vascular puncture, and the methods for delivering such a device. Example embodiments of a delivery device according to the present invention are shown in FIGS. 1, 2, 3, and 4. The descriptions refer to "vessels" for convenience; the present invention is applicable to facilitate closure of various types of tissue openings. Example embodiments of a gripping device according to the present invention are shown in FIGS. 4, 5, and 6. Methods for placing the device are shown in FIG. 7. Example embodiments of the closure cincture are shown in FIG. 8.

FIG. 1(a,b) is a schematic illustration of a cincture delivery sheath 101 according to the present invention. FIG. 1(a) shows the cincture 102 before contraction, and FIG. 1(b) shows the cincture 102 after contraction. The interior wall of the delivery sheath 101 delivers a cincture 102, which can be held in place in the sheath 101 by a retention structure 103. The retention structure 103 can prevent the cincture 102 from malpositioning and from prematurely contracting. The cincture 102 can be held by fingers from the retention structure 103, can be sufficiently rigid to not readily change position, or can be temporarily held in place by a wax-like or other semi-solid biocompatible material that will give way with contraction of the cincture 102. The cincture 102 can be attached to a retractable suture loop 106 which is contained in a lumen 104, shown in the figure as a cylindrical structure. The lumen 104 can comprise a narrowed portion 105 that permits the cincture material to pass, but prevents a tightening feature (e.g., a functional slipknot) from passing. Thus when the suture loop 106 is pulled, the radius of the cincture 102 becomes narrower. When the suture loop 106 is pulled in its entirety, the cincture loop 102 completely closes, effecting closure of the opening (e.g., a puncture wound).

FIG. 2(a,b) is a schematic illustration of a cincture delivery sheath 201 according to the present invention. The embodiment of FIG. 2 comprises a cincture 202 external to a sheath 201. FIG. 2(a) shows the cincture 202 before contraction; FIG. 2(b) shows the cincture 202 after contraction. The wall of the delivery sheath 201 delivers an external cincture 202 which is held in place on the sheath by a retention structure 203, which prevents the cincture 202 from malpositioning or premature tightening. The cincture 202 can be held by fingers from the retention structure 203, can be sufficiently rigid to not readily change position, or can be temporarily held in place by a wax-like or other semi-solid biocompatible material that will give way with contraction of the cincture 202. The cincture 202 is attached to a retractable suture loop 206 which is contained in a lumen 204, here shown as a cylindrical structure. The lumen 204 can comprise a portion with a reduced cross-section 205 or similar feature that allows cincture material or suture to pass, but prevents a tightening feature (e.g., a functional slip-knot) from passing. Thus when the suture loop 206 is pulled, the cincture 202 is pulled down the external surface of the sheath 201, and the radius of the cincture 202 becomes narrower. When the suture loop 206 is pulled in its entirety, the cincture loop 202 completely closes, effecting closure of the opening.

Figure 3B:
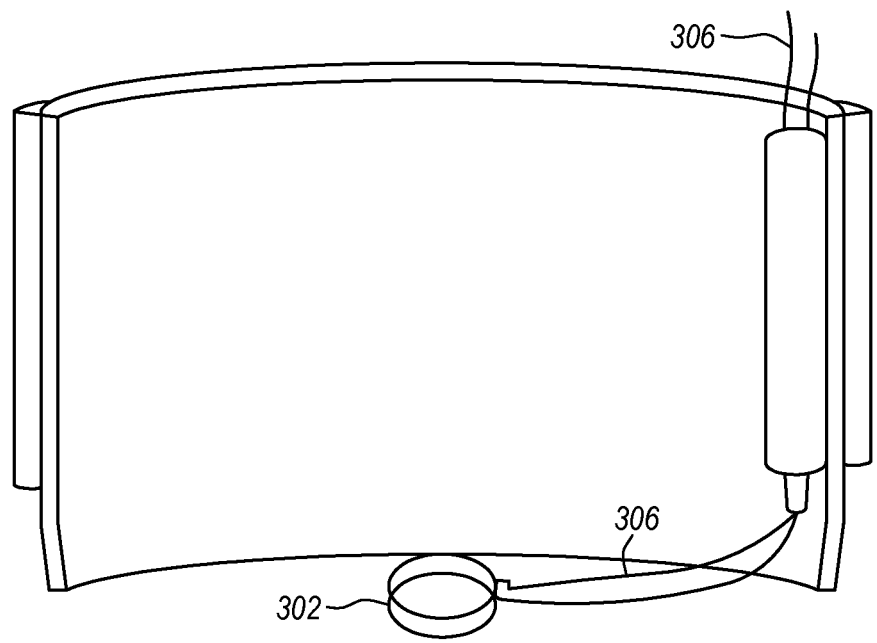
Figure 5A:
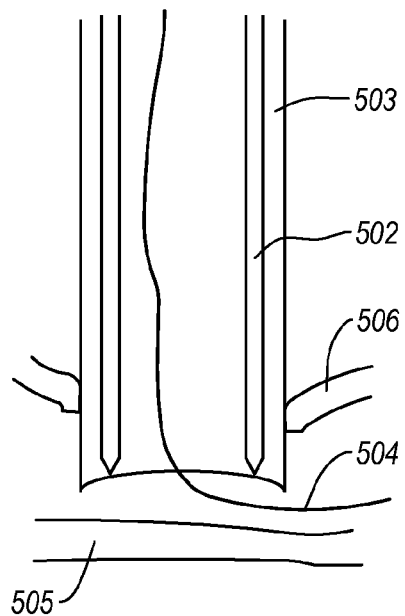
FIG. 5(a,b,c,d) is a schematic illustration of eversion of the edges of a tissue opening, and closure of the opening, according to the present invention.
Figure 5B:
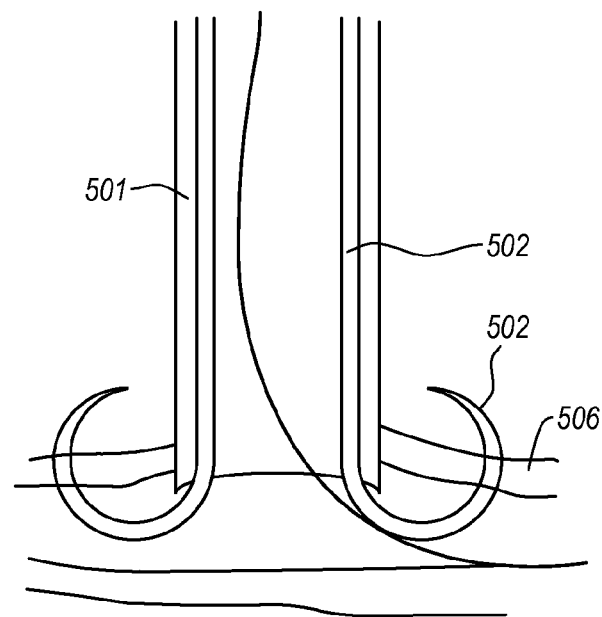
Figure 5C:
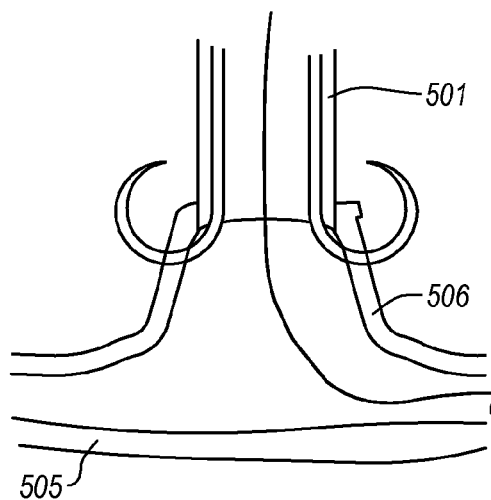
Figure 5D:
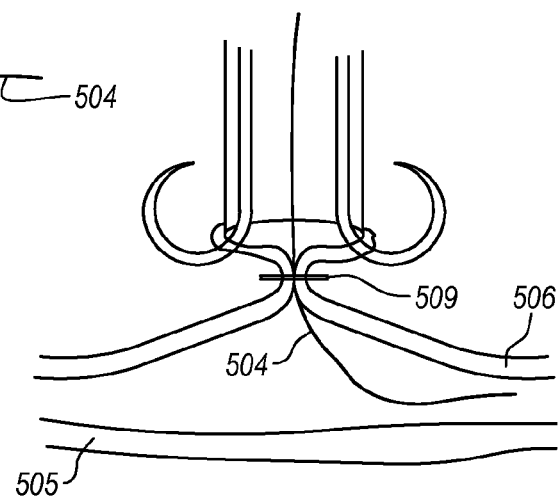
Figure 6A:
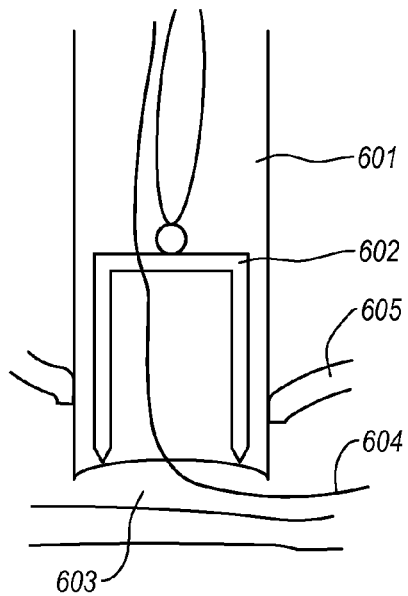
FIG. 6(a,b,c,d) is a schematic illustration of eversion of the edges of a tissue opening, and closure of the opening, according to the present invention.
Figure 6B:
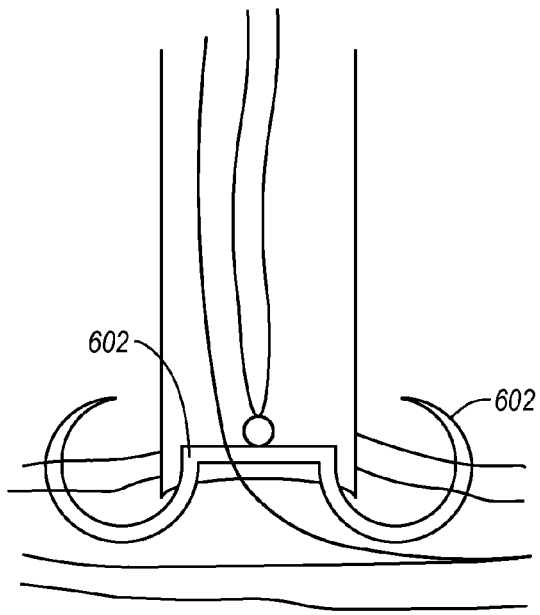
Figure 6C:
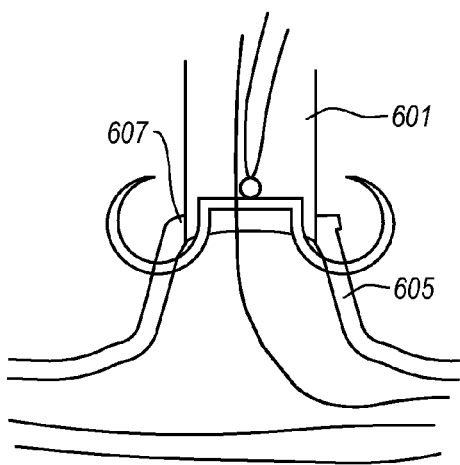
Figure 6D:
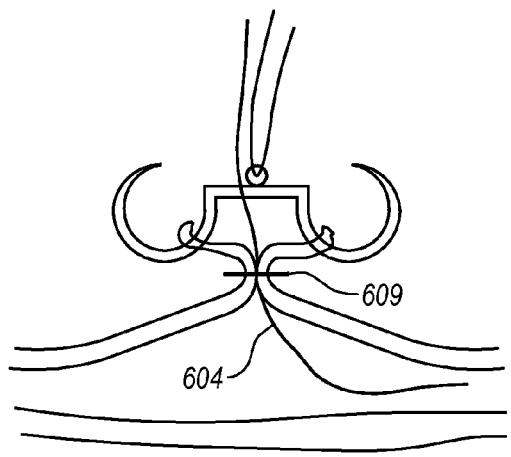

FIG. 3(a,b) is a schematic illustration of a cincture delivery sheath 301 according to the present invention The embodiment of FIG. 3 comprises a cincture 302 external to the sheath 301. FIG. 3(a) shows the cincture 302 before contraction; FIG. 3(b) shows the cincture 302 after contraction. The wall of the delivery sheath 301 delivers an external cincture 302 which can be held in place on the sheath 301 by a retention structure 303. The retention structure 303 can comprise, as examples, fingers projecting from the sheath 301, a second sheath engaged with the first sheath 301, or a wax-like or other semi-solid biocompatible material that will give way with contraction of the cincture. The cincture 302 comprises a resilient or memory material that it is self-contracting after removal from the sheath 301. The cincture can be attached to a retractable suture loop 306 which is contained in a lumen 304, here shown as a cylindrical structure. The retractable suture loop 306 can be used to pull the cincture 203 past the end of the sheath 301. If the retention structure 303 comprises a second sheath, or otherwise has the ability to move the cincture past the end of the sheath 301, then the suture loop 306 might not be necessary (although it can still be useful for retrieving misplaced cinctures). When the self contracting cincture 302 is moved past the end of the sheath 301, by action of the suture loop 306 or the retention device 303, the cincture contracts, reducing its radius and closing the opening in the tissue.

Tissue edge eversion can be accomplished with a gripper or everter device such as that shown in FIG. 4. FIG. 4(a,b) is a schematic illustration of a gripper and sheath, shown in section to illustrate gripper tines disposed within the sheath 403. Gripper tines 402 (two in the figure, although more or fewer can be used) are disposed within a sheath 403 in FIG. 4a. The sheath 403 constrains the gripper tines 402 to fit within the walls of the sheath 403. In FIG. 4b, the gripper tines 402 have moved past the end of the sheath 403. Absent the constraining influence of the sheath 403, the gripper tines 402 have curved outwards from the sheath and upwards along the direction of the sheath. The gripper tines can grip the edges of a tissue opening, and evert them when the gripper tines or the corresponding sheath is pulled away from the tissue.

FIG. 5(a,b,c,d) is a schematic illustration of eversion of the edges of a tissue opening using a device such as that described in relation to FIG. 4, and closure of the opening using a cincture such as those described above. FIG. 5a shows the device with the gripper tines 502 constrained in a sheath 503. A guidewire 504 passes through the sheath 503. The sheath 503 is resident in the tissue opening, passing through the proximal vessel wall 506 but not reaching the distal vessel wall 505. FIG. 5b shows the device after the gripper tines 502 have been extended past the end of the sheath 503. The gripper tines 502, have curved away from the sheath 503 and back along the direction of the sheath 503, penetrating the proximal vessel wall 506. Traction applied to the gripper tines 502 and sheath 503 everts the edges of the opening, as shown in FIG. 5c. The edges are held by the gripper tines 502 so that the proximal vessel wall 506 is pulled when the gripper tines 502 and sheath 503 are pulled. The everted edges of the tissue opening are now ready for deployment of a cincture like those described herein with respect to FIGS. 1-3 and 8, shown in FIG. 5(d) by reference numeral 509.

FIG. 6(a,b,c,d) is a schematic illustration of a method of everting the edges of a tissue opening, using a device like that described in relation to FIG. 4 and closing the opening with a cincture such as those described herein with respect to FIGS. 1-3 and 8. The gripper sheath 601 with memory tines 602 is introduced into a blood vessel 603 over a guidewire 604. After introduction, the tines 602 are extended, which then grip the proximal tissue 605. Traction (pulling) is placed on the gripper sheath 602, everting the wound edges 607. A cincture 609 can be placed over the everted wound edges, closing the puncture wound around the guidewire 604. If there is no bleeding, then the guidewire 604 and sheath 601 can be removed.

FIG. 7(a,b,c,d,e,f,g) is a schematic illustration of steps in a method of closing a tissue opening according to the present invention. In FIG. 7a, a gripper sheath 701, for example a gripper sheath like that described in relation to FIG. 4, is present within an opening in tissue, near a proximal wall 706 and edges 705 of an opening therethrough, but not near a distal wall 707. The gripper sheath 701 constrains gripper tines 702 disposed within the gripper sheath 701. A guidewire 704 passes through the gripper sheath 701. In FIG. 7b, the gripper tines 702 have been extended past the end of the gripper sheath 701, curving back and engaging the edges 705 of the tissue opening. In FIG. 7c, the gripper sheath 701 has been pulled away from the tissue. The edges 705 of the opening, held by the gripper tines 702, have been everted by the motion of the gripper sheath 701. The gripper tines can reside within sublumens within or on the sheath, or a single shared lumen in the sheath. The number of gripper tines can be 2 or greater, and they can be directed away from the lumen or cross over each other. They can penetrate the blood vessel wall, but need not fully penetrate the vessel, instead simply gripping the vessel wall so it can be everted. The tines can be extended by pushing or by a specialized instrument that provides suitable extension such as a gun-like or syringe-like plunger configuration.

Figure 7A:
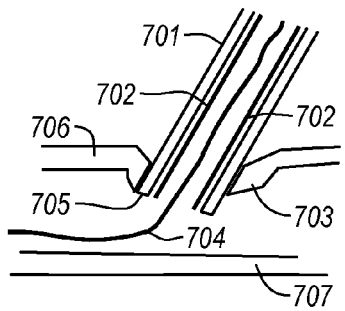
FIG. 7(a,b,c,d,e,f,g) is a schematic illustration of steps in a method of closing a tissue opening according to the present invention.
Figure 7B:
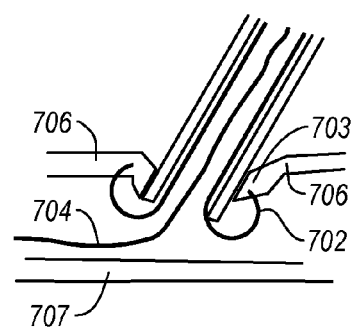
Figure 7C:
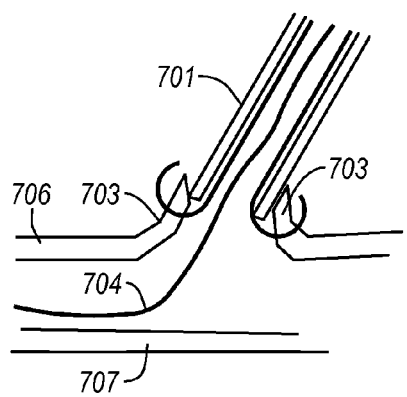
Figure 7D:
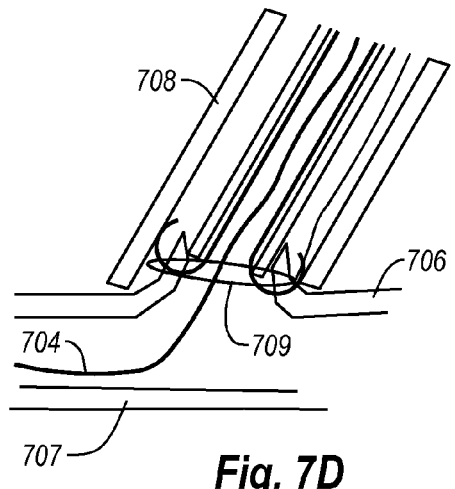
Figure 7E:
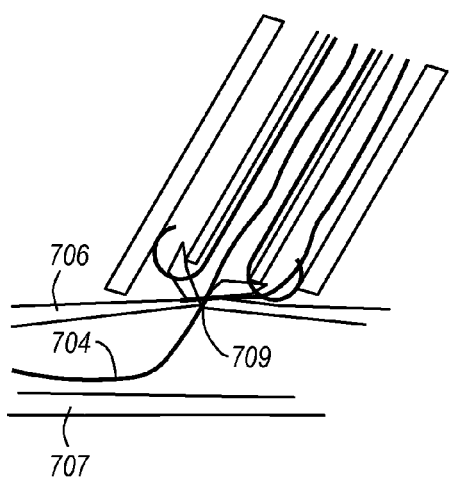
Figure 7F:
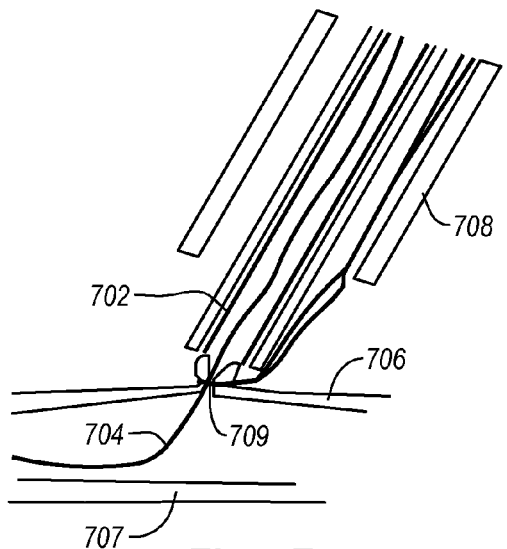
Figure 7G:
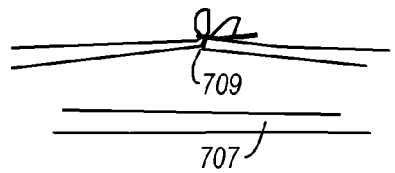
Figure 8:
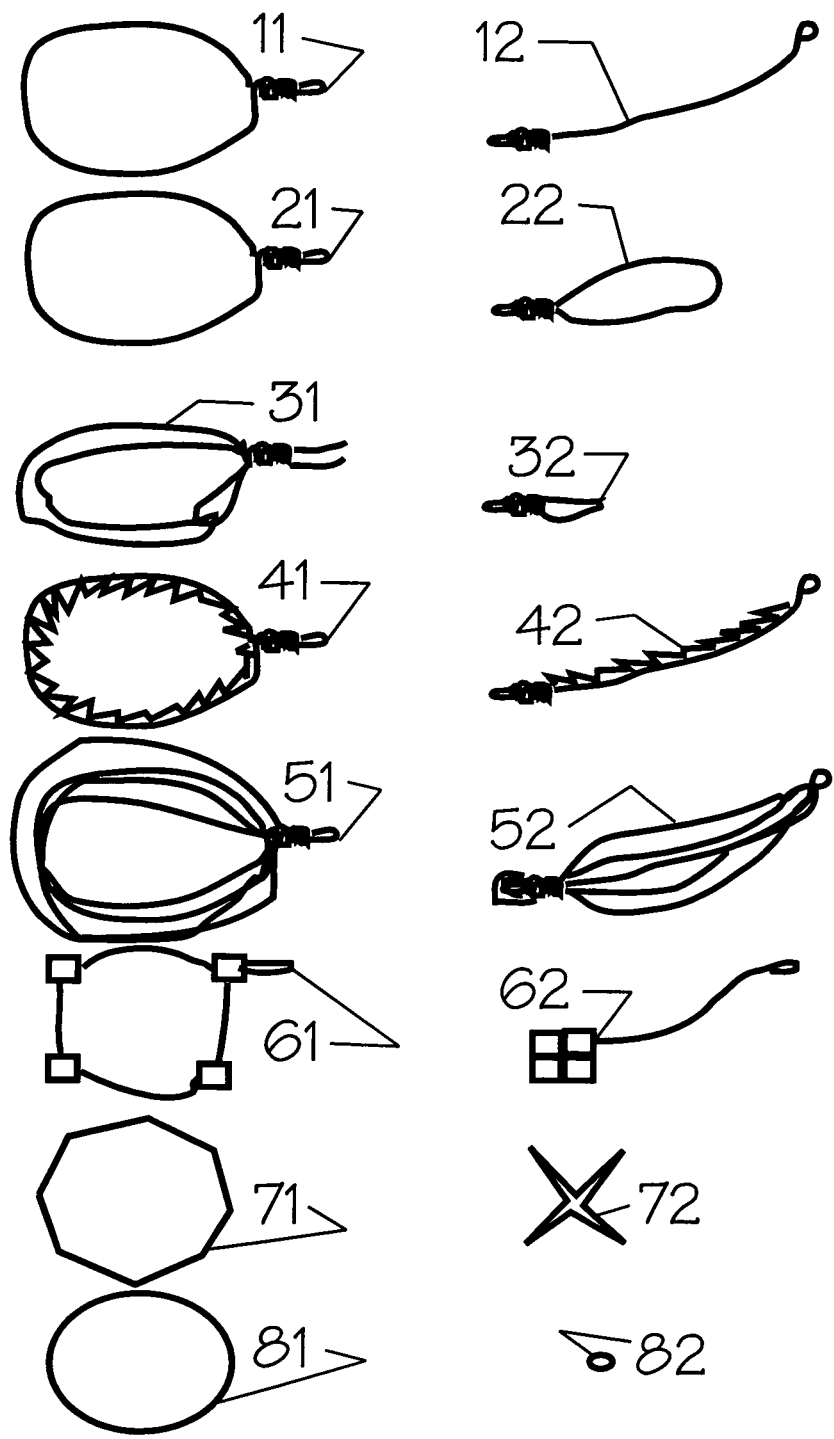
FIG. 8 is a schematic illustration of several cinctures suitable for use in the present invention.

In FIG. 7d a cincture 709 like those described herein, such as those described with respect to FIGS. 1-3 and 8, is advanced to the tissue opening using a second sheath 708. The cincture 709 and sheath can comprise an internal cincture or external cincture, both described elsewhere herein, such as those described with respect to FIGS. 1-3 and 8. The cincture 709 can be advanced from the second sheath 708, and tightened over the everted edges of the opening, as shown in FIG. 7(e). The second sheath 708 can be removed, leaving the opening closed by the cincture 709, as shown in FIG. 7(f). The gripper tines 702 can also be retracted into the gripper sheath 701, all as shown in FIG. 7(f). The suture loop 706 (if required), gripper tines 702 and gripper sheath 701, and second sheath 708 can all be removed, leaving the cincture 709 in place closing the opening, as shown in FIG. 7(g).

FIG. 8 comprises schematic depictions of various embodiments of closure cinctures suitable for use in the present invention. 11 is a simple cincture with a slip-knot, with only one suture end to be pulled and distal loop for the pulling suture, 12 shows the cincture completely closed. 21 is a cincture with a slip knot device, with both suture ends to be pulled through the slip knot device, resulting in a loop of material when the cincture is completely closed, as shown in 22. 31 is a cincture composed of a loop and the pulling suture is functionally internal to the cincture initially, resulting in very little trailing material when the cincture is completely closed, as shown in 32. 41 demonstrates a cincture that closes by the use of dentates on the cincture so that it can lock when the cincture is closed, as shown in 42. 51 is a cincture made of multiple strands of material, resulting in a multiple level complex closed cincture, as shown in 52. 61 is a cincture with beads or other geometric structures or grippers that fit together and hold the wound closed with the cincture is closed, as shown in 62. 71 is a cincture made of memory material in the shape of an octagon, so that when pushed off the delivery sheath contracts to a four point star cincture, as shown in 72. 81 is a cincture made of a rubber-like or memory material, that when pushed off of the delivery sheath, contracts uniformly and closes the cincture, as shown in 82.

Examples of knots that can be suitable for use with the present invention include, but are not limited to, the overhand knot or half knot, the double overhand knot, the multifold-overhand-knot, the Flemish eight, hitches (single simple, half, clove, two half, buntline, rolling Magnus, midshipmans tautline, adjustable jamming, cow, reversed half, lobster buoy), single loops (bowline, Dutch marine bowline, cowboy bowline, double figure-of-eight loop, flamish eight, bowstring knot, tucked double overhand, butterfly loop, lineman's loop, artillery loop, pendant hitch), clove hitch, reef knot, square knot, noose (simple noose, strangle-snare, scaffold knot, gallows knot, hangman's knot, reverse eight-noose), monkey fist, the dolly, fisherman's bend, surgeon's knot, sheet bend knot, timber hitch, fisherman's knot, reef knot, square knot, DuraKnot, sliding knots, simple sliding knot, Nicky's knot, Roeder's knot, Seoul Medical Centre knot, Smith & Nephew's knot, Tennesee's knot, purse string, and surgical knot with extra loop. Other knots and cincture devices could also be used and are anticipated. Endoscopic knot tying devices and suture cutting devices can also be used to create the cincture for this device and are also anticipated.

Examples of suture material that can be suitable for use with the present invention include, but are not limited to, absorbable, non-absorbable, braided, monofilament, pseudo-monofilament, multifilament, barbed, smooth, directional, and bidirectional. The suture material can be composed of but not limited to polyglycolic acid, polydioxanon, polylactate, polycaprone, silk, linen, cotton, treated and non-treated collagen, "catgut", chromic, Vicryl, Monocyrl, PDS, polyester, polypropylene, polyamide, stainless steel, and others.

The tines or gripping portion of a gripper sheath or components of sheath or cincture device can be made from any number of suitable materials, including radioopaque materials and materials coated to be made radioopaque, including bioabsorbable polymers or compounds, non-absorbable alloys and compounds including stainless steel, MP35, Nitinol, Nickel-Titanium ally, Kevlar, nylon polyester acrylic, gold, platinum, tantalum, niobium, molybdenum, rhodium, palladium silver, hafnium, tungsten, iridium. Materials with memory can be useful to allow tines to spontaneously open after extended from the sheath. These can be made in the form of wires, fibers, filaments, small beams, and other extruded, woven, or formed shapes. Piano wire, super elastic memory wire, chromium allows, alloys of titanium and nickel, and other elastic memory materials previously mentioned as well as others can be used as well The cincture device can be made from a number of suitable materials, including typical suture materials, flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, co-polymers of these or other polymers, or drug-embedded or drug-eluting polymers to prevent coagulation or intimal hyperplasia (such as Taxol), also which can be made radioopaque by markers and addition of appropriate radiopaque materials.

EXAMPLE EMBODIMENTS

The present invention can comprise a device to close puncture wounds caused by catheter procedures and especially angiography comprised cincture, snare, or noose-like device that in the introduction state resides in or on a sheath, and after either being expelled from the sheath or contracted spontaneously or by the use of a pulling suture loop, closes the cincture or noose, closing the wound. In order to allow the cincture to be placed, a gripping device is used that has tines that assumes a planar or conical or other shape, engages vessel wall by means of tissue hooks or penetrators, is pulled, and everts and holds the edges of the vessel wound or puncture so the cincture can be placed.

The gripping device can have single or multiple hooks, arms, gripping members, or purchase or penetrating devices to engage and seize the vessel wall. Each hook or gripper can be a single or multiple hook, toothed, textured, penetrating, or gripping structure. The gripping device can have a minimal of 2 members (or tines) that are linear, curvilinear, spiral, leaf-like, diamond shaped, woven, or other complex shapes, but still function as an opening-closing structure that can be extended, grip the vessel wall, and then after the cincture is placed, be retracted.

The resident gripping device can have members that are coated or backed with a fabric or membrane, either completely or partially. The resident gripping device or cincture can elute therapeutic material to prevent thrombogenesis, hemorrhage, inflammation, and intimal hyperplasia with vascular closure. The device can be used in angiography, angioplasty, vascular puncture, tissue biopsy, or trauma that cause a puncture wound that should be closed. The gripping device or cincture can comprise materials with memory, so that the device spontaneously assumes it therapeutic shape when expelled from the sheath. The gripping device can comprise at least 2 or more members; 3 or more members can be preferable in some applications.

A tissue opening can be closed according to the present invention by a) introducing a guidewire and then gripping sheath, b) penetrating the proximal surface of the blood vessel by the gripping sheath over the guidewire, c) gripping the blood vessel by extending the tines, d) putting a cincture delivery sheath over the gripping sheath, e) pulling gripping sheath against the tissue wall (e.g., the blood vessel wall), seating the grippers in the tissue and everting the wound edges, f) closing the cincture over the everted wound edges, g) removing the gripping tines and sheath, h) if no bleeding occurs, i) removing the guidewire, j) cutting the loop of string, leaving the cincture device safely seated on the external surface of the blood vessel with the puncture repaired. Alternatively, after the knot or cincture has been closed, the material or suture could be cut with an endoscopic suture cutter. Also, the guidewire could be removed before the gripping device, which would permit a tighter knot or cincture, and this is also anticipated.

A tissue opening can be closed according to the present invention employing a dedicated device consisting of gripping device, a sheath to deliver a cincture or knot device or knot tying device, placing the cincture over the gripping device and everted blood vessel wall, and closing the puncture wound with this cincture, noose-like device, or knot.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A tissue closure device for closing an aperture in a wall of tissue, comprising:
   a) a delivery sheath having a first end configured to be advanced towards and contact the wall of tissue to surround the aperture and a second end spaced from the first end in a direction along a longitudinal length of the delivery sheath;
   b) a cincture element, removably mounted to the delivery sheath, defining an opening that has a first size when the cincture element is mounted to the delivery sheath, and can assume a second size, smaller than the first, when the cincture element is not mounted to the delivery sheath, the cincture element having a first end, a second end, an intermediate portion disposed between the first end and the second end and forming the opening, and a knot associated with the cincture element;
   c) a cincture-retaining structure near the first end of the delivery sheath; and
   d) a cylindrical member disposed within the delivery sheath, and having a lumen therethrough, the cylindrical member having a distal end distal the cincture-retaining structure and closer to the first end than the second end of the delivery sheath when the cincture element has the first size, the cylindrical member, and the lumen thereof, being configured to receive the first end and second end of the cincture element through the lumen and prevent passage of the knot.

2. A tissue closure device as in claim 1, wherein the delivery sheath defines an inner cross section, where the cincture element mounts with and is urged to the first size by the cincture-retaining structure.

3. A tissue closure device as in claim 2, wherein the cincture-retaining structure comprises a ridge extending from the sheath into the inner cross section.

4. A tissue closure device as in claim 2, wherein the knot accommodates transition of the cincture element from the first size to the second size and resists transition of the cincture element from the second size to the first size.

5. A tissue closure device as in claim 4, wherein the cincture element comprises a flexible elongated element, and wherein the knot comprises a slipknot tied in the elongated element.

6. A tissue closure device as in claim 5, wherein the cincture element comprise a suture, line, string, or wire.

7. A tissue closure device as in claim 1, wherein the delivery sheath defines an outer cross section near a first end thereof, wherein the cincture element mounts with the delivery sheath.

8. A tissue closure device as in claim 7, wherein the delivery sheath comprises a cincture-retaining structure that discourages motion of the cincture element relative to the delivery sheath way from the first end of the delivery sheath.

9. A tissue closure device as in claim 8, wherein the cincture-retaining structure comprises one or more elements mounted with or formed as part of the delivery sheath.

10. A tissue closure device as in claim 7, wherein the knot accommodates transition of the cincture element from the first size to the second size and resists transition of the cincture element from the second size to the first size.

11. A tissue closure device as in claim 10, wherein the cincture element comprises a flexible elongated element, and the knot comprises a slipknot tied in the elongated element.

12. A tissue closure device as in claim 11, wherein the cincture element comprise a suture, line, string, or wire.

13. A device as in claim 7, wherein the delivery sheath comprises a lumen that can accommodate a gripping device and guidewire.

14. A tissue closure device as in claim 1, wherein the cincture element assumes the second size absent an externally applied force.

15. A device as in claim 1, wherein the delivery sheath comprises a lumen that can accommodate a gripping device and guidewire.

16. A tissue closure device for closing an aperture in a wall of tissue, comprising:
   a) a delivery sheath having a first end configured to be advanced towards and contact the wall of tissue to surround the aperture and a second end spaced from the first end in a direction along a longitudinal length of the delivery sheath;
   b) a cincture element, removably mounted to an exterior surface of the delivery sheath, having a first end, a second end, an intermediate portion disposed between the first end and the second end and forming an opening, and a knot associated with the cincture element, the opening continued to have a first size when the cincture element is mounted with the delivery sheath, and can assume a second size, smaller than the first, when the cincture element is not mounted with the delivery sheath;
   c) a cincture retention structure near the first end of the delivery sheath and being configured to selectively retain the cincture element, the cincture retention structure disposed inside of the lumen of the delivery sheath in a pre-deployed position with the cincture element having the first size; and
   d) a cylindrical member disposed within a lumen of the delivery sheath adjacent to the cincture retention structure, at a location off axis from a longitudinal axis of the delivery sheath in a direction transverse to the longitudinal axis and adjacent an inner surface of the delivery sheath, with the cylindrical member having a narrowed distal end distal the cincture retention structure and closer to the first end than the second end of the delivery sheath when the cincture element has the first size, and having a lumen therethrough, the cylindrical member, and the lumen thereof, being configured to receive the first end and second end of the cincture element through the lumen and prevent passage of the knot.

17. A tissue closure device as in claim 16, wherein the delivery sheath defines an inner cross section, and has a cincture-retaining structure near a first end of the delivery sheath.

18. A tissue closure device as in claim 16, wherein the knot accommodates transition of the cincture element from the first size to the second size and resists transition of the cincture element from the second size to the first size.

19. A tissue closure device as in claim 16, wherein the delivery sheath defines an outer cross section near a first end thereof, wherein the cincture element mounts with the delivery sheath.

20. A tissue closure device as in claim 16, further comprising a cincture-retaining structure that comprises one or more elements mounted with or formed as part of the delivery sheath.

21. A tissue closure device for closing an aperture in a wall of tissue, comprising:
  a) a delivery sheath having a lumen and having a first end configured to be advanced towards and contact the wall of tissue to surround the aperture and a second end spaced from the first end in a direction along a longitudinal length of the delivery sheath;
  b) a cincture element, removably mounted to an exterior surface of the delivery sheath, having a first end, a second end, an intermediate portion disposed between the first end and the second end and forming an opening, and a knot associated with the cincture element, the opening formed by the cincture element having a first size when the cincture element is mounted to the delivery sheath, and can assume a second size, smaller than the first, when the cincture element is not mounted to the delivery sheath;
  c) a cincture retention structure near the first end of the delivery sheath and being configured to selectively retain the cincture element, the cincture retention structure disposed outside of the lumen of the delivery sheath in a pre-deployed position with the cincture element having the first size; and
  d) a cylindrical member disposed within the lumen of the delivery sheath at a location laterally off axis from a longitudinal axis of the delivery sheath and adjacent an inner surface of the delivery sheath, with the cylindrical member having a narrowed distal end distal the cincture retention structure and closer to the first end than the second end of the delivery sheath when the cincture element has the first size, and having a lumen therethrough, the cylindrical member, and the lumen thereof, being configured to receive the first end and second end of the cincture element through the lumen and prevent passage of the knot.

22. The tissue closure device as in claim 21, wherein the cincture retention structure comprises a wax-like or other semi-solid biocompatibility material configured to give way under contraction of the cincture element.

23. The tissue closure device as in claim 21, wherein the cincture retention structure comprises a second sheath engaging with delivery sheath.

24. The tissue closure device as in claim 21, wherein the cincture element is formed from a resilient or memory material.

* * * * *